United States Patent [19]
Micetich et al.

[11] Patent Number: 4,668,514

[45] Date of Patent: * May 26, 1987

[54] PENICILLIN DERIVATIVES

[75] Inventors: Ronald G. Micetich, Alberta, Canada; Shigeru Yamabe, Kobe; Motoaki Tanaka; Tomio Yamazaki, both of Tokushima; Naobumi Ishida, Naruto; Makoto Kajitani, Tokushima, all of Japan

[73] Assignee: Taiho Pharmaceutical Company Limited, Tokyo, Japan

[*] Notice: The portion of the term of this patent subsequent to Dec. 31, 2002 has been disclaimed.

[21] Appl. No.: 658,373

[22] Filed: Oct. 5, 1984

[30] Foreign Application Priority Data

Oct. 13, 1983 [JP] Japan .................. 58-192040
Apr. 9, 1984 [JP] Japan .................. 59-71499
Apr. 18, 1984 [JP] Japan .................. 59-78064

[51] Int. Cl.$^4$ .................. C07D 499/00; A61K 31/425
[52] U.S. Cl. .................. 424/114; 540/310; 540/304; 514/192; 514/195
[58] Field of Search .................. 260/245.2 R, 245.2 T; 514/192, 195; 424/114; 540/304, 310

[56] References Cited

U.S. PATENT DOCUMENTS 4,507,239 3/1985 Micetich et al. ............. 260/245.2 R
4,562,073 12/1985 Micetich et al. ............. 514/192

Primary Examiner—Nicholas S. Rizzo
Attorney, Agent, or Firm—Murray and Whisenhunt

[57] ABSTRACT

This invention provides a penicillin derivative of the formula

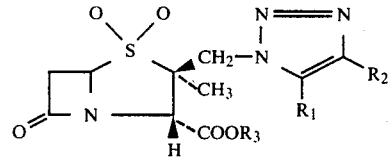

wherein $R_1$ and $R_2$ are the same or different and represent hydrogen, $C_{1-6}$ alkyl, $C_{1-6}$ hydroxyalkyl, $C_{3-9}$ acyloxyalkyl, $C_{8-13}$ benzyloxyalkyl, $C_{2-7}$ alkoxyalkyl, $C_{2-7}$ alkoxycarbonyl, $C_{3-8}$ alkenyloxycarbonyl, $C_{3-8}$ alkynyloxycarbonyl, phenyl, amino, cyano, formyl, trifluoromethyl, $C_{2-6}$ acyl, carbamoyl, $C_{2-7}$ alkylcarbamoyl, benzyloxycarbonylamino, $C_{2-7}$ alkoxycarbonylamino; and $R_3$ is hydrogen, a group for forming a pharmaceutically acceptable salt, or a penicillin carboxyl protecting group, with the proviso that both of $R_1$ and $R_2$ are not hydrogen or $C_{2-7}$ alkoxycarbonyl at the same time and that when one of $R_1$ and $R_2$ is hydrogen, the other is not $C_{2-7}$ alkoxycarbonyl, or a pharmaceutically acceptable acid addition salt, process for preparing the derivative, and a pharmaceutical composition containing the derivative.

14 Claims, No Drawings

PENICILLIN DERIVATIVES

This invention relates to penicillin derivatives and to a process for preparing them.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve satisfactory effects against some types of microorganisms because of resistance of the microorganism to the β-lactam type antibiotics. The resistance thereof are usually attributable to β-lactamase produced by the microorganism. The β-lactamase is an enzyme which acts to cleave the β-lactam ring of the β-lactam type antibiotic, thereby causing the antibiotic to lose its antimicrobial activity. For this reason, the action of β-lactamase must be eliminated or inhibited so as to enable the β-lactam type antibiotic to produce satisfactory effects. The elimination or inhibition of the β-lactamase activity can be achieved by β-lactamase inhibitors, which are used conjointly with the β-lactam type antibiotic to increase the antimicrobial activity of the antibiotic.

It is an object of the present invention to provide novel compounds having β-lactamase inhibitory action.

It is another object of the invention to provide processes for preparing the same.

It is a further object of the invention to provide a pharmaceutical composition having excellent β-lactamase inhibitory action.

It is an object of the invention to provide compositions which, when combined with β-lactam type antibiotics, can increase the antibacterial activity of the antibiotics.

The penicillin derivatives of the present invention are represented by the formula

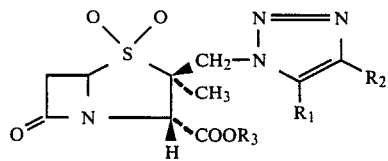

wherein $R_1$ and $R_2$ are the same or different and represent hydrogen, $C_{1-6}$ alkyl, $C_{1-6}$ hydroxyalkyl, $C_{3-9}$ acyloxyalkyl, $C_{8-13}$ benzyloxyalkyl, $C_{2-7}$ alkoxyalkyl, $C_{2-7}$ alkoxycarbonyl, $C_{3-8}$ alkenyloxycarbonyl, $C_{3-8}$ alkynyloxycarbonyl, phenyl, amino, cyano, formyl, trifluoromethyl, $C_{2-6}$ acyl, carbamoyl, $C_{2-7}$ alkylcarbamoyl, benzyloxycarbonylamino, $C_{2-7}$ alkoxycarbonylamino, and $R_3$ represents hydrogen, a group for forming a pharmaceutically acceptable salt or penicillin carboxyl-protecting group, with the proviso that $R_1$ and $R_2$ are not hydrogen or $C_{2-7}$ alkoxycarbonyl at the same time and that when one of $R_1$ and $R_2$ is hydrogen, the other is not $C_{2-7}$ alkoxycarbonyl.

A preferred class of compounds of the invention includes those wherein $R_1$ and $R_2$ represent hydrogen, $C_{1-6}$ alkyl, phenyl, $C_{2-6}$ acyl, trifluoromethyl, carbamoyl, $C_{2-7}$ alkylcarbamoyl, $C_{2-7}$ alkoxyalkyl, cyano, formyl, $C_{3-8}$ alkenyloxycarbonyl or $C_{3-8}$ alkynyloxycarbonyl.

Another preferred class of compounds of the invention includes those wherein $R_1$ and $R_2$ represent $C_{1-6}$ alkyl, $C_{2-7}$ alkoxycarbonyl, $C_{1-6}$ hydroxyalkyl, $C_{3-9}$ acyloxyalkyl, $C_{8-13}$ benzyloxyalkyl or phenyl.

Yet another preferred class of the compounds of the invention includes those wherein one of $R_1$ and $R_2$ represents hydrogen and the other represents amino, $C_{2-7}$ alkoxycarbonylamino or benzyloxycarbonylamino.

The most preferred class of the compounds of the invention includes those wherein $R_1$ and $R_2$ represent hydrogen, $C_{1-6}$ alkyl, $C_{1-6}$ hydroxyalkyl, amino, carbamoyl, $C_{2-7}$ alkylcarbamoyl or $C_{2-6}$ acyl.

The present invention does not include a compound wherein both $R_1$ and $R_2$ represent hydrogen or $C_{2-7}$ alkoxycarbonyl or a compound wherein one of $R_1$ and $R_2$ is hydrogen and the other is $C_{2-7}$ alkoxycarbonyl.

Examples of $C_{1-6}$ alkyl groups represented by $R_1$ and $R_2$ in the formula (I) are straight-chain or branched-chain alkyl such as methyl, ethyl, propyl, butyl, isobutyl, pentyl, hexyl, and the like. Examples of $C_{1-6}$ hydroxyalkyl groups are straight-chain or branched-chain hydroxyalkyl such as hydroxymethyl, hydroxyethyl, hydroxyisopropyl, hydroxybutyl, hydroxyhexyl, and the like. Examples of $C_{3-9}$ acyloxyalkyl groups are acetyloxymethyl, propionyloxymethyl, butyryloxymethyl, acetyloxyethyl, propionyloxyethyl, valeryloxyethyl, caproyloxyethyl, acetyloxypropyl, and the like. Examples of $C_{8-13}$ benzyloxyalkyl groups are benzyloxymethyl, benzyloxyethyl, benzyloxypropyl, benzyloxybutyl, benzyloxypentyl, benzyloxyhexyl, etc. Examples of $C_{2-7}$ alkoxyalkyl groups are methoxymethyl, ethoxymethyl, propyloxymethyl, butoxymethyl, methoxyethyl, ethoxyethyl, propyloxyethyl, butoxyethyl, etc. Examples of $C_{2-7}$ alkoxycarbonyl groups are methoxycarbonyl, ethoxycarbonyl, propyloxycarbonyl, butoxycarbonyl, hexyloxycarbonyl, etc. Examples of $C_{3-8}$ alkenyloxycarbonyl groups are allyloxycarbonyl, butenyloxycarbonyl, pentenyloxycarbonyl, hexenyloxycarbonyl, etc. Examples of $C_{3-8}$ alkynyloxycarbonyl groups are propynyloxycarbonyl, butynyloxycarbonyl, pentynyloxycarbonyl, hexynyloxycarbonyl, etc. Examples of $C_{2-6}$ acyl groups are acetyl, propionyl, butyryl, valeryl, isobutyryl, etc. Examples of $C_{2-7}$ alkylcarbamoyl groups are methylcarbamoyl, ethylcarbamoyl, propylcarbamoyl, butylcarbamoyl, pentylcarbamoyl, isopropylcarbamoyl, t-butylcarbamoyl, etc. Examples of $C_{2-7}$ alkoxycarbonylamino groups are methoxycarbonylamino, ethoxycarbonylamino, propyloxycarbonylamino, isopropyloxycarbonylamino, butoxycarbonylamino, t-butoxycarbonylamino, penyloxycarbonylamino, hexyloxycarbonylamino, etc.

With respect to $R_3$, examples of the group for forming a pharmaceutically acceptable salt include; sodium, potassium, lithium, or like alkali metal atoms; calcium, magnesium or like alkaline earth metal atoms; cyclohexylamine, trimethylamine, diethanolamine or like organic amine residues; alginine, lysine or like basic amino acid residues; ammonium residues, etc. The penicillin carboxyl-protecting groups from esters which are well-known for protecting penicillin carboxyl groups in the syntheses or esters which are hydrolyzed in vivo. Examples of these esters or protecting groups for forming the esters include any of those described in Japanese Unexamined Patent Publication (Kokai) No. 81380/1974 and H. E. Flynn, "Cephalosporins and Penicillins, Chemistry and Biology" (published in 1972 by Academic Press). Specific examples thereof are straight- or branched-chain $C_{1-6}$ alkyl such as methyl, ethyl, propyl, isopropyl, tert-butyl, pentyl, hexyl and the like; $C_{2-7}$ alkoxymethyl such as methoxymethyl, ethoxymethyl, propyloxymethyl, isopropyloxymethyl, butoxymethyl and hexyloxymethyl; $C_{3-10}$ alkylcarbonyloxyalkyl such as methylcarbonyloxymethyl, ethylcarbonyloxymethyl, butylcarbonyloxymethyl and hexylcarbonyloxymethyl, methylcarbonyloxyethyl, ethylcarbonyloxyethyl, butylcarbonyloxyethyl, pivaloyloxyethyl, methylcarbonyloxypropyl, ethylcarbonyloxypropyl, pivaloyloxypropyl; ($C_{5-7}$ cycloalkyl)-carbonyloxymethyl such as cyclopentylcarbonyloxymethyl, cyclohexylcarbonyloxymethyl and cycloheptylcarbonyloxymethyl; $C_{9-14}$ benzylcarbonyloxyalkyl such as benzylcarbonyloxymethyl, benzylcarbonyloxyethyl, benzylcarbonyloxypropyl and benzylcarbonyloxybutyl; $C_{3-8}$ alkoxycarbonylmethyl such as methoxycarbonylmethyl, ethoxycarbonylmethyl, propyloxycarbonylmethyl and hexyloxycarbonylmethyl; $C_{4-9}$ alkoxycarbonylethyl such as methoxycarbonylethyl, ethoxycarbonylethyl, propyloxycarbonylethyl, butoxycarbonylethyl and hexyloxycarbonylethyl; halogenated $C_{1-6}$ alkyl substituted with 1 to 3 halogen atoms such as chloromethyl, 2,2-dibromoethyl and trichloroethyl; $C_{1-6}$ alkoxy- or nitro-substituted or unsubstituted benzyl such as p-methoxybenzyl, p-ethoxybenzyl, o-nitrobenzyl and p-nitrobenzyl; (5-$C_{1-6}$ alkyl or phenyl-substituted or unsubstituted-2-oxo-1,3-dioxoden-4-yl)methyl such as (2-oxo-1,3-dioxoden-4-yl)methyl, (5-methyl-2-oxo-1,3-dioxoden-4-yl)methyl and (5-phenyl-2-oxo-1,3-dioxoden-4-yl)methyl; $C_{8-13}$ benzoyloxyalkyl such as benzoyloxymethyl, benzoyloxyethyl, benzoyloxypropyl and benzoyloxybutyl; benzyloxy-$C_{1-4}$ alkyl such as benzyloxymethyl, benzyloxyethyl and benzyloxybutyl; dimethyl chlorosilyl; trichlorosilyl; dimethylaminoethyl; etc.

The ester residues represented by $R_3$ include both carboxyl-protecting groups acceptable in the synthesis of penicillin compounds and pharmaceutically acceptable ester residues. A pharmaceutically acceptable ester having such residue is an ester which is easily hydrolyzed in vivo and which is a non-poisonous ester capable of rapidly decomposing in the blood or tissue of humans, thereby producing the corresponding acid of the formula (I) in which $R_3$ is hydrogen atom. Generally in the synthesis of penicillin compounds, ester-protecting groups are used in the art to protect penicillin carboxyl groups or other carboxyl groups. While it is difficult to determine which ester-protecting group should be used, consideration are usually given to select esters in which the protecting group per se is sufficiently stable in the reaction and which does not permit cleavage of the β-lactam ring in removal of the ester-protecting groups. Most commonly used as such ester-protecting groups are p-nitrobenzyl group, benzhydryl group, trichloroethyl group, trichlorosilyl group, tetrahydropyranyl group, etc. Examples of the pharmaceutically acceptable ester groups are phthalidyl, crotonolacton-4-yl, γ-butyrolacton-4-yl, (2-oxo-1,3-dioxoden-4-yl)methyl etc.

The compounds of the invention wherein at least one of $R_1$ and $R_2$ represents amino group can form a pharmaceutically acceptable acid addition salt when reacted with an appropriate inorganic acid such as hydrochloric acid, hydrobromic acid, sulfuric acid or phosphoric acid, or with an appropriate organic acid such as propionic acid, acetic acid, citric acid, lactic acid, tartaric acid. The present invention also includes these pharmaceutically acceptable acid addition salts.

The penicillin derivatives and the pharmaceutically acceptable acid addition salt thereof of the present invention are all novel compounds and have β-lactamase inhibitory properties, hence useful as β-lactamase inhibitory agents.

The penicillin derivatives of the invention, when used in combination with a known β-lactam type antibiotic, can increase the antimicrobial activity of the β-lactam type antibiotic.

Examples of antibiotics which can be used conjointly with the compounds of the present invention are β-lactam antibiotics which exhibit antibacterial action against gram-positive and/or gram-negative bacteria and which include commonly used penicillins such as ampicillin, amoxicillin, hetacillin, ciclacillin, mecillinam, carbenicillin, sulbenicillin, ticarcillin, piperacillin, apalcillin, methicillin, mezlocillin and pharmaceutically acceptable salts thereof; esters of penicillins such as bacampicillin, carindacillin, talampicillin, carfecillin, and pivmecillinam; cephalosporins such as cephaloridine, cephalothin, caphapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil, cephaloglycin, and pharmaceutically acceptable salts thereof. The β-lactam antibiotics are usually used in an amount of about 0.1 to about 10 parts by weight, preferably about 0.2 to about 5 parts by weight, per part by weight of the compound of the invention.

Although the penicillin derivative of the present invention and the β-lactam antibiotic can be separately administered, it is preferable that the derivative of the invention is mixed with the β-lactam antibiotic to form an anti-bacterial composition which may be orally or parenterally administered. Thus the derivatives of the formula (I) can be used for treating infectious disease of mammals including humans.

The composition of the present invention may be made into preparations for oral administration, such as tablets, pills, capsules, granules, powders, syrups, lozenges, solutions, suspensions, etc., or into preparations for parenteral administrations, such as aqueous, suspending or water-soluble preparations for intravenous, subcutaneous or intramuscular injections.

Carriers useful in formulating the preparations are commonly used pharmaceutically acceptable non-toxic carriers such as gelatin, lactose, starch, magnesium stearate, talc, vegetable oil, animal oil, polyalkylene glycol, crystalline cellulose, corn starch, hydroxypropyl cellulose, etc. The carrier may be used with other additives such as diluents, binders, buffer agents, preservatives, glazes, disintegrators, coating agents, etc.

The daily dose of the preparation can be appropriately determined and may depend on species, physical conditions, administration methods and many other factors. However, this judgement is well within the skill of the medical art. The amount is usually decided based on the β-lactamase inhibitory effective amount of the derivative of the formula (I). Preferably the daily dose is such that the total amount of the present compound and β-lactam antibiotic is about 1 to about 200 mg/Kg body weight for oral administration and about 1 to about 100 mg/Kg body weight for parenteral administration.

The penicillin derivatives of the formula (I) according to the present invention can be prepared, for example, by the processes as shown below in reaction equations.

Reaction Equation-1

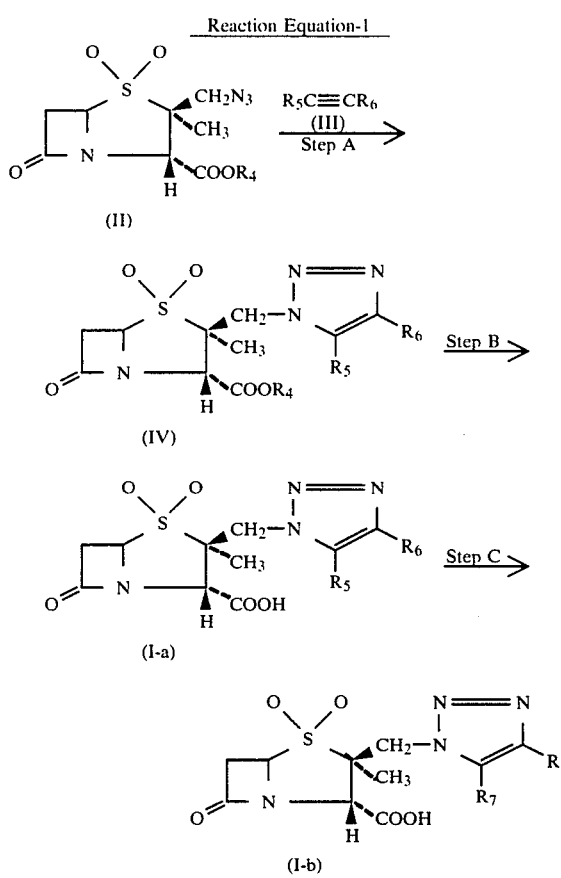

In the foregoing formulae, $R_4$ is a penicillin carboxyl protecting group, $R_5$ and $R_6$ are hydrogen, $C_{1-6}$ alkyl, $C_{3-9}$ acyloxyalkyl, $C_{8-13}$ benzyloxyalkyl, $C_{2-7}$ alkoxyalkyl, $C_{2-7}$ alkoxycarbonyl, $C_{3-8}$ alkenyloxycarbonyl, $C_{3-8}$ alkynyloxycarbonyl, phenyl, cyano, formyl, trifluoromethyl, $C_{2-6}$ acyl, carbamoyl or $C_{2-7}$ alkylcarbamoyl, and $R_7$ and $R_8$ are both $C_{1-6}$ hydroxyalkyl or one of them is $C_{1-6}$ hydroxyalkyl while the other is the same group as $R_5$ or $R_6$. Both of $R_5$ and $R_6$ are not hydrogen or $C_{2-7}$ alkoxycarbonyl at the same time or when one of $R_5$ and $R_6$ is hydrogen, the other is not $C_{2-7}$ alkoxycarbonyl.

Examples of the penicillin carboxyl protecting groups represented by $R_4$ include known groups such as those disclosed in Japanese Unexamined Patent Publication (Kokai) No.81380/1974 and H. E. Flynn, "Cephalosporins and Penicillins, Chemistry and Biology" (published in 1972 by Academic Press). Specific examples of the groups $R_4$ are substituted or unsubstituted alkyl groups such as methyl, ethyl, propyl, butyl, tert-butyl and trichloroethyl; substituted or unsubstituted aralkyl groups such as benzyl, diphenyl methyl and p-nitrobenzyl; acyloxyalkyl groups such as acetoxymethyl, acetoxyethyl, propionyloxyethyl, pivaloyloxyethyl, pivaloyloxypropyl, benzoyloxymethyl, benzoyloxyethyl, benzylcarbonyloxymethyl and cyclohexylcarbonyloxymethyl; alkoxyalkyl and aralkyloxyalkyl groups such as methoxymethyl, ethoxymethyl and benzyloxymethyl; and other groups such as tetrahydropyranyl, dimethylaminoethyl, dimethylchlorosilyl and trichlorosilyl.

Steps A, B and C of the foregoing process are described below in detail.

Step A

A penicillanic acid derivative of the formula (II) is reacted with an acetylene derivative of the formula (III) to provide a compound of the formula (IV). The reaction is conducted in a suitable solvent by reacting a penicillanic acid derivative of the formula (II) with a known acetylene derivative of the formula (III) in an amount of about 1 to about 50 moles, preferably about 1 to about 10 moles, per mole of the derivative of the formula (II). Solvents useful in this reaction include an acetylene derivative of the formula (III) as used in an excess amount or aromatic hydrocarbon such as benzene, xylene and toluene, ether such as tetrahydrofuran and dioxane, polar solvent such as acetone or the like which will not adversely affect the reaction. The reaction is conducted at a temperature of between about 50° C. and the boiling point of the solvent, or at 50° to 200° C. in a sealed tube. The reaction generally goes to completion in about 2 hours to about 2 weeks. Depending on the kind of the penicillin carboxyl protecting group represented by $R_4$, the compounds of the formula (IV) thus obtained may or may not be the esters of the penicillin derivatives of the formula (I) which can be hydrolyzed in vivo. If desired, the compounds of the formula (IV) may be subjected to the de-esterification as described below in Step B to form a derivative of the formula (I-a) which, when required, is converted in the usual manner to a pharmaceutically acceptable salt or different ester thereof. Alternatively, the compound of the formula (IV) can be made into an ester or a pharmaceutically acceptable salt of the formula (I-a) by a conventional ester interchange or salt-forming reaction.

The compound of the formula (II) to be used as the starting material in Step A is a novel compound undisclosed in literature and can be synthesized by the method described in Japanese Patent Application No. 69142/1982 (relating to an invention accomplished by us. See also Unexamined Japanese Patent Publication (Kokai) No. 185589/1983 published on Oct. 29, 1983). The disclosed method comprises the steps of reacting a metal azide with a known derivative of penicillanic acid of the formula

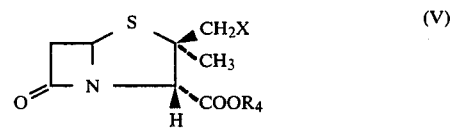

wherein X represents chlorine atom or bromine atom and $R_4$ is as defined above, and oxydizing the reaction mixture.

The foregoing method will be described below in detail. The reaction between the compound of the formula (V) and the metal azide is conducted in a suitable solvent by using the metal azide in an amount of about 1 to about 50 moles, preferably about 1 to about 10 moles, per mole of the compound of the formula (V). Examples of the metal azides which can be used include those commonly used, such as sodium azide, potassium azide and like azides of alkali metals, and barium azide and like azides of alkaline earth metals. Useful solvents are not particularly limited as far as they do not adversely affect the reaction. Examples of useful solvents are dimethylformamide, ethyl acetate, acetone, dichloromethane, tetrahydrofuran, dioxane, methanol, ethanol and like organic solvents. These organic solvents can be used singly or in mixtures. Also a mixture of such solvent and water is usable. The reaction proceeds at a temperature of usually about −20° to about 100° C., preferably about 0° to about 100° C. The resulting product can be used in subsequent oxidation without isolation, or alternatively after isolation and purification by a conventional method. The oxidation subsequent to the azide-forming reaction is conducted by using an oxidizing agent commonly employed such as permanganic acid, periodic acid, peracetic acid, performic acid, trifluoroperacetic acid, perbenzoic acid, m-chloroperbenzoic acid, hydrogen peroxide, etc. The oxidizing agent can be used in large excess, and may be employed preferably in an amount of about 1 to about 2 moles per mole of the starting compound. The oxidation is carried out usually in a suitable solvent. Useful solvents include any of those which do not adversely affect the oxidation reaction such as chloroform, pyridine, tetrahydrofuran, dioxane, methylene chloride, carbon tetrachloride, acetic acid, formic acid, dimethylformamide, water, etc. The oxidation is performed at a temperature which is not particularly limited but generally ranges from room temperature to cooling temperature, preferably about 0° to about 30° C. The process for preparing the compound of the formula (II) is described in detail in Reference Example to be set forth later.

The compounds of the formula (V) and their preparation are disclosed in Japanese Unexamined Patent Publication (Kokai) No. 4788/1983 published on Jan. 11, 1983.

Step B

The compound of the formula (IV) is subjected to de-esterification without or after isolation from the reaction mixture obtained in Step (A), thereby giving a penicillin derivative of the formula (I-a).

The de-esterification method which can be employed includes various conventional methods such as reduction, treatment with an acid and hydrolysis which permits the conversion of a carboxyl protecting group to a carboxyl group. It is preferred to carry out the reduction when the carboxyl protecting group $R_4$ is trichloroethyl, benzyl, p-nitrobenzyl, diphenylmethyl or the like. A treatment with an acid is advantageously carried out when the carboxyl protecting group is 4-methoxybenzyl, tert-butyl, trityl, diphenylmethyl, methoxymethyl, tetrahydropyranyl or the like. If the carboxyl-protecting group is an active ester, the reaction frequently proceeds with ease under mild hydrolysis conditions or by merely bringing the ester into contact with water.

The reduction can be effected by using a mixture of (a) a metal such as zinc or zinc-amalgam and/or a chromium salt such as chromium chloride or chromium acetate and (b) an acid, e.g. formic acid or acetic acid. The reduction can also be conducted by catalytic hydrogenation in a solvent. Examples of catalysts useful in the catalytic reduction are platinum, platinum oxide, palladium, palladium oxide, palladium-barium sulfate, palladium-calcium carbonate, palladium-carbon, nickel oxide, Raney-nickel and the like. Solvents which can be used in the reduction are not particularly limited so far as they do not adversely affect the reaction. Examples of useful solvents include alcohols such methanol and ethanol; ethers such as tetrahydrofuran and dioxanes; esters such as ethyl acetate; fatty acids such as acetic acid; and a mixture of these solvents with water.

Examples of acids which can be used for converting the carboxyl protecting group to carboxyl group are lower fatty acids such as formic acid and acetic acid; trihalogenated acetic acids such as trichloroacetic acid and trifluoroacetic acid; hydrohalogenic acids such as hydrochloric acid and hydrofluoric acid; organic sulfonic acids such as p-toluenesulfonic acid and trifluoromethanesulfonic acid; and mixtures of these acids. When a liquid acid is used, the reaction can proceed without a solvent. However, it is possible to use a solvent which will not adversely affect the reaction. Examples of such solvents are dimethylformamide, dichloromethane, chloroform, tetrahydrofuran, acetone or the like.

The penicillin derivative of the formula (I-a) thus obtained in the form of free acid according to the present invention can be transformed into the desired pharmaceutically acceptable salt or ester thereof by the salt-forming or esterification reaction conventionally employed in the art.

In preparing a compound wherein the ester residue is, for example, 3-phthalidyl, crotonolacton-4-yl or γ-butyrolacton-4-yl, the penicillin derivative of the formula (I-a) can be esterified with 3-halogenated phthalide, 4-halogenated crotonolactone, 4-halogenated-γ-butyrolactone or the like. Suitable halogen atoms of the foregoing halides include chlorine, bromine, iodine and the like. The reaction is carried out by dissolving a salt of the penicillin derivative of the formula (I-a) in a suitable polar organic solvent such as N,N-dimethylformamide and adding an approximately equimolecular amount of the halogenated compound to the solution. The reaction temperature ranges generally from 0° to about 100° C., preferably from about 15° to about 35° C. Suitable salts of the penicillin derivative to be used in the esterification are salts of alkali metals such as sodium and potassium and salts of tertiary amines such as triethylamine, ethyldiisopropylamine, N-ethylpiperidine, N,N-dimethylaniline and N-methylmorpholine. After completion of the reaction, the desired compound can be easily seprated by a conventional method.

Step C

The compound of the formula (I-a) wherein at least one of $R_5$ and $R_6$ is $C_{8-13}$ benzyloxyalkyl is subjected to debenzylation reaction (i.e., a reaction to eliminate benzyl group) as it is or as isolated from the reaction mixture obtained in Step B, thereby giving a penicillin derivative of the formula (I-b) as contemplated in the present invention. This dibenzylation can be conducted by a conventional catalytic reduction or method using an acid. The catalytic reduction is performed by use of a catalyst in a suitable solvent. Examples of catalysts useful in the catalytic reduction are platinum, platinum oxide, palladium, palladium oxide, palladium-barium sulfate, palladium-calcium carbonate, palladium-carbon, nickel oxide, Raney-nickel and the like. Useful solvents include alcohols such as methanol and ethanol; ethers such as tetrahydrofuran and dioxane; esters such as ethyl acetate; fatty acids such as acetic acid; and a mixture of these solvents with water.

Examples of acids which can be used in the method using an acid are lower fatty acids such as formic acid and acetic acid; trihalogenated acetic acids such as trichloroacetic acid and trifluoroacetic acid; hydrohalogenic acids such as hydrochloric acid and hydrofluoric acid; organic sulfonic acids such as p-toluenesulfonic acid and trifluoromethanesulfonic acid; and mixtures of these acids. When aliquid acid is used, the reaction can proceed without a solvent. However, it is possible to use a solvent which will not adversely affect the reaction. Examples of such solvents are dimethylformamide, dichloromethane, chloroform, tetrahydrofuran, acetone or the like.

The reaction in Step C can proceed simultaneously with the de-esterification in Step B if the latter is conducted by a catalytic reduction or a treatment with an acid.

The penicillin derivative of the formula (I-b) thus obtained according to the present invention can be transformed in the same manner as in the conversion of the penicillin derivative of the formula (I-a) into the desired pharmaceutically acceptable salt or ester. In preparing a compound wherein the ester residue is, for example, 3-phthallidyl, crotonolacton-4-yl or γ-butyrolacton-1-yl, the pencillin derivative of the formula (I-b) can be esterified in the same manner as in the treatment of the derivative of the formula (I-a).

The contemplated product, the penicillin derivative or its salt or ester of the present invention obtained in the reaction in each step is separated from the reaction mixture after completion of the reaction and collected by a conventional method and, when required, can be purified by e.g., recrystallization, thin layer chromatography, column chromatography, and the like.

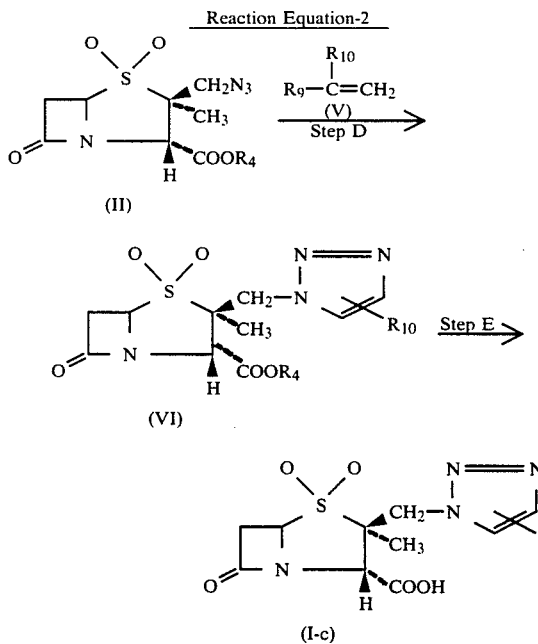

compound of the formula (VI) is produced. The reaction is conducted in a suitable solvent, using the vinyl derivative of the formula (V) in an amount of about 1 to about 500 moles, preferably about 1 to about 200 moles, per mole of the penicillanic acid derivative of the formula (II). Usable as the solvent are a vinyl derivative of the formula (V) as used in excess amount or any solvents which do not adversely affect the reaction, e.g., aromatic hydrocarbons such as benzene, toluene and xylene, ethers such as tetrahydrofuran and dioxane, etc. Preferably the reaction is carried out at a temperature of between 50° C. and the boiling point of the solvent or at 50° to 200° C. in a sealed tube. The reaction is completed generally in about 2 hours to about 2 weeks. Depending on the kind of the penicillin carboxyl protecting group $R_4$ in the compound of the formula (VI), the compound of the formula (VI) thus obtained may or may not be the ester of the pencillin derivative of the formula (I) which will be hydrolyzed in vivo. When required, the compound of the formula (VI) may be subjected to the de-esterification as described below in Step E to form a derivative of the formula (I-c) which, when required, is converted by the usual method into a pharmaceutically acceptable salt or ester. The compound of the formula (VI) can also be transformed by a conventional salt-forming or ester interchange reaction directly into a pharmaceutically acceptable salt or ester as defined in the present invention.

Step E

The compound of the formula (VI) is subjected to de-esterification as contained in the reaction mixture or as isolated from the reaction mixture, giving a penicillin derivative of the formula (I-c). The de-esterification is conducted under the same conditions as in Step B.

The pencillin derivative of the formula (I) according to the present invention can also be prepared, for example, by the process as shown below in reaction equation.

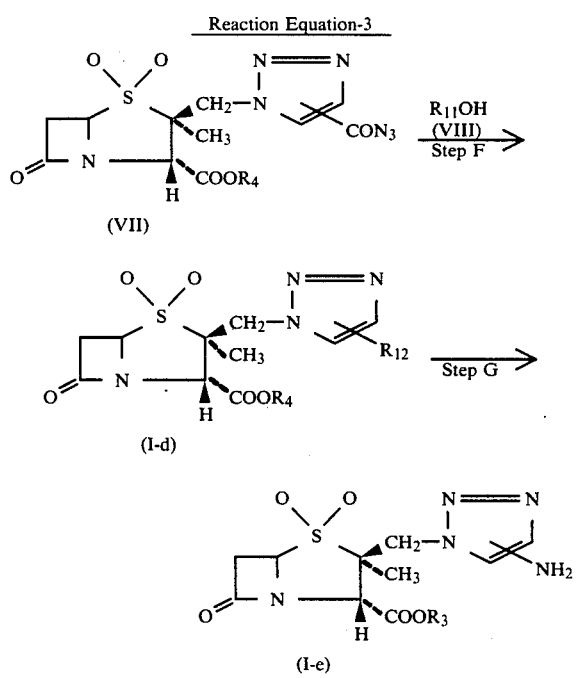

In the foregoing formulae, $R_4$ is as defined above, $R_9$ is $C_{2-5}$ acyloxy or benzoyloxy and $R_{10}$ is $C_{1-6}$ alkyl.

Examples of the $C_{2-5}$ acyloxy groups represented by $R_9$ are acetoxy, propionyloxy, butyryloxy, valeryloxy and the like. Examples of the $C_{1-6}$ alkyl groups represented by $R_{10}$ are straight chain and branched chain alkyl such as methyl, ethyl, propyl, butyl, isobutyl, pentyl and hexyl.

Of the compounds of the formula (I) according to the present invention, the compound of the formula (I-c) wherein one of $R_1$ and $R_2$ is hydrogen while the other is $C_{1-6}$ alkyl can be prepared also by the process as shown above in Reaction Equation-2. The steps in Reaction Equation 2 are carried out as described below in detail.

Step D

The penicillanic acid derivative of the formula (II) is reacted with the vinyl derivative of the formula (V), whereby the $C_{2-5}$ acyloxy or benzoyloxy group represented by $R_9$ in the formula (V) is eliminated and a In the foregoing formulae, $R_3$ and $R_4$ are as defined above, $R_{11}$ is $C_{1-6}$ alkyl or benzyl and $R_{12}$ is $C_{2-7}$ alkoxycarbonylamino or benzyloxycarbonylamino.

The steps in the aforesaid reaction equation are practiced as set forth below in detail.

Step F

The penicillanic acid derivative of the formula (VII) is reacted with the alcohol of the formula (VIII) to produce the present penicillin derivative of the formula (I-d). Examples of the $C_{1-6}$ alkyl groups represented by $R_{11}$ in the foregoing formula (VIII) are straight chain or branched chain alkyl such as methyl, ethyl, isopropyl, butyl, t-butyl and hexyl. Examples of the $C_{2-7}$ alkoxycarbonylamino groups represented by $R_{12}$ are methoxycarbonylamino, ethoxycarbonylamino, propyloxycarbonylamino, isopropyloxycarbonylamino, butoxycarbonylamino, t-butoxycarbonylamino, pentyloxycarbonylamino, hexyloxycarbonylamino, etc.

The reaction is conducted in a solvent under nitrogen atmosphere with reflux for about 0.5 to about 5 hours using the alcohol of the formula (VIII) in an amount of about 1 to about 10 moles per mole of the derivative of the formula (VII). Useful solvents include ethers such as diethyl ether, tetrahydrofuran; aromatic hydrocarbons such as benzene and toluene; halogenated hydrocarbons such as dichloromethane and chloroform. The compound of the formula (VII) can be prepared by reacting a compound of the formula (IX)

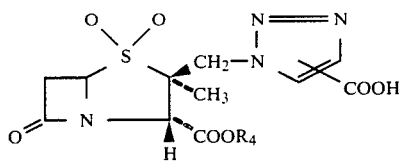

(IX)

wherein $R_4$ is as defined above with a halogenating agent to form an acid halide, and then reacting the acid halide with an azide such as tetrabutyl ammonium azide or a metal azide, e.g., sodium azide. The halogenating agents used in the halogenation reaction include thionyl chloride, phosphorus oxychloride, phosphorus trichloride, phosphorus tribromide, phosphorus pentachloride, phosgene, oxalyl chloride, and the like. The halogenation reaction is usually conducted in a solvent and, if required, in the presence of a base. Useful solvents include ethers such as diethyl ether, tetrahydrofuran and the like; aromatic hydrocarbons such as benzene, toluene, and the like; halogenated hydrocarbons such as dichloromethane, chloroform, and the like. Some of the halogenating agents may also act as the solvent. The bases used when required include organic tertiary amines such as triethylamine or the like. The reaction is preferably conducted at a temperature between about 0° C. and a boiling temperature of the solvent for about 0.5 to about 5 hours. The subsequent reaction with the azide is usually conducted in a suitable solvent using the resulting acid halide as contained in the reaction mixture or as isolated from the reaction mixture. The solvents used in the foregoing halogenation reaction can be used as the solvent in this reaction. This reaction is conducted at about 0° C. to about 40° C. for about 0.5 to about 5 hours. The compound of the formula (VII) produced by the foregoing method can be used in the reaction without purification.

Depending on the kind of the penicillin carboxyl protecting group $R_4$ in the compound of the formula (I-d), the compound of the formula (I-d) thus obtained may or may not be the ester of the penicillin derivative of the formula (I) which will be hydrolyzed in vivo. If desired, the compound of the formula (I-d) can be made directly into an ester as defined in the present invention by the conventional ester interchange reaction.

Step G

The compound of the formula (I-d) is subjected to catalytic reduction in a solvent to provide a penicillin derivative of the formula (I-e). The catalytic reduction is carried out in a conventional manner. Examples of catalysts useful in the catalytic reduction are platinum, platinum oxide, palladium, palladium oxide, palladium-barium sulfate, palladium-calcium carbonate, palladium-carbon, nickel oxide, Raney-nickel, and the like. Solvents which can be used in the reduction are not particularly limited so far as they do not adversely affect the reaction. Examples of useful solvents include alcohols such as methanol and ethanol; ethers such as tetrahydrofuran and dioxane; esters such as ethyl acetate; fatty acids such as acetic acid; and a mixture of these solvents with water.

When using a compound (I-d) in which the penicillin carboxyl protecting group $R_4$ is benzyl, p-nitrobenzyl or diphenylmethyl, the reaction gives a compound in the form of a free acid ($R_3=H$) which, in turn, can be converted into the desired pharmaceutically acceptable salt or ester by the salt-forming or ester interchange reaction conventionally employed in the art. In preparing the compound of the present invention esterified with, for example, 3-phthalidyl, crotonolacton-4-yl or γ-butyrolacton-4-yl, the penicillin derivative of the formula (I-d) wherein $R_4$ is hydrogen or (I-e) wherein $R_3$ is hydrogen can be esterified with 3-halogenated-phthalide, 4-halogenated-crotonolactone or 4-halogenated-γ-butyrolactone. Examples of useful halogen atoms of the foregoing halogenated compounds are chlorine, bromine and iodine. The reaction is carried out by dissolving a salt of the penicillin derivative of the formula (I-d) or (I-e) in a suitable polar organic solvent such as N,N-dimethylformamide and adding an approximately equimolecular amount of a halogenated compound to the solution. The reaction temperature ranges generally from about 0° to about 100° C., preferably from about 15° to about 35° C. Suitable salts of the penicillin derivative of the formula (I-d) or (I-e) to be used in the esterification are salts of alkali metals such as sodium and potassium and salts of tertiary amines such as triethylamine, ethyldiisopropylamine, N-ethylpiperidine, N,N-dimethylaniline and N-methylmorpholine. After completion of the reaction, the desired compound can be easily separated from the reaction mixture by a conventional method. When required, the penicillin derivative of the formula (I-d) or the formula (I-e) wherein $R_3$ is not hydrogen may be subjected to de-esterification to give a corresponding free acid which, when required, is converted by a conventional method into a pharmaceutically acceptable salt or ester. The derivative of the formula (I-d) or (I-e) can also be converted by a conventional salt-forming or ester interchange reaction directly into a pharmaceutically acceptable salt or ester as defined in the present invention.

The contemplated product, the penicillin derivative or its salt or ester of the present invention, thus obtained in the reaction in each step is separated, after completion of the reaction, from the reaction mixture and collected by a conventional method and, when required, can be purified by recrystallization, thin layer chromatography, column chromatography or other method.

The compounds of the formula (IX) serving as the starting material in the foregoing process are novel compounds undisclosed in literature and can be prepared, for example, by the process as described below in Reference Example 2.

Given below are Examples and Reference Examples for a better understanding of the present invention.

REFERENCE EXAMPLE 1

Preparation of p-nitrobenzyl 2β-azidomethyl-2α-methylpenam-3α-carboxylate 1,1-dioxide A 32.5 g quantity of sodium azide was dissolved in 160 ml of water and 200 ml or N,N-dimethylformamide. To the solution was added dropwise at 0° to 5° C. a solution of 37.1 g of p-nitrobenzyl 2β-chloromethyl-2α-methylpenam-3α-carboxylate in 300 ml of N,N-dimethylformamide. After the addition, the mixture was stirred at room temperature for 3.5 hours. Ice water was poured into the reaction mixture and the mixture was extracted with ethyl acetate. The ethyl acetate layer was washed with a saturated aqueous solution of sodium chloride and dried over anhydrous magnesium sulfate. The ethyl acetate was distilled off under reduced pressure, giving p-nitrobenzyl 2β-azidomethyl-2α-methylpenam-3α-carboxylate as a residual oil.

The p-nitrobenzyl 2β-azidomethyl-2α-methylpenam-3α-carboxylate thus obtained was dissolved in 1.5 liters of acetic acid and 250 ml of water. To the solution was added 24.0 g of potassium permanganate at 0° to 5° C. over a period of 30 minutes and the mixture was agitated at room temperature for 4 hours. An aqueous solution of hydrogen peroxide was added until the reaction mixture became colorless. Water was added thereto and the mixture was extracted with chloroform. The chloroform layer was washed successively with water, an aqueous solution of sodium hydrogen carbonate and a saturated aqueous solution of sodium chloride and dried over anhydrous magnesium sulfate. The chloroform was distilled off under reduced pressure. The residue was purified by silica gel column chromatography, giving 26.6 g of the title compound as an amorphous product in a yield of 65%.

Infrared absorption spectrum (KBr): $v_{max}(\text{cm}^{-1}) = 2120, 1770$.

Nuclear magnetic resonance spectrum (CDCl$_3$): δ (ppm) = 1.42 (3H, s), 3.45–3.60 (2H, m), 3.75 (1H, d), 3.96 (1H, d), 4.56–4.75 (1H, m), 4.64 (1H, s), 5.33 (2H, s), 7.56 (2H, d), 8.26 (2H, d).

REFERENCE EXAMPLE 2

Preparation of benzhydryl 2β-(4-carboxy-1,2,3-triazol-1-yl)methyl-2α-methylpenam-3α-carboxylate 1,1-dioxide Benzhydryl 2β-azidomethyl-2α-methylpenam-3α-carboxylate 1,1-dioxide (0.50 g) and acetylenecarboxylic acid (0.083 g) were agitated in 2 ml of dichloromethane at room temperature under nitrogen atmosphere for 24 hours. The solvent was removed by distillation under reduced pressure. Benzene was added to the residual oil and the insolubles were filtered. Hexane was added to the residue and the precipitated crystals were filtered, giving 0.23 g of the title compound as white crystals melting 120° to 121° C.

Infrared absorption spectrum (KBr): $v_{max}(\text{cm}^{-1}) = 1805, 1745$.

Nuclear magnetic resonance spectrum (CDCl$_3$): δ (ppm) = 1.07 (3H, s), 3.2–3.8 (2H, m), 4.5–4.7 (1H, m), 4.69 (1H, s), 5.12 (2H, bs), 7.02 (1H, s), 7.1–7.6 (10H, m), 8.33 (1H, s).

EXAMPLE 1

Preparation of p-nitrobenzyl 2β-(4,5-dimethyl-1,2,3-triazol-1-yl)methyl-2α-methylpenam-3α-carboxylate 1,1-dioxide (Compound 1)

A 3.0 g quantity of p-nitrobenzyl 2β-azidomethyl-2α-methylpenam-3α-carboxylate 1,1-dioxide, 1.1 g of 2-butyne and 20 ml of benzene were reacted in a sealed tube at 110° C. for 100 hours. The reaction mixture was concentrated under reduced pressure and the residue was purified by silica gel column chromatography, giving 0.54 g of the title compound as an amorphous product (hereinafter referred to as "Compound 1").

Infrared absorption spectrum (KBr): $v_{max}(\text{cm}^{-1}) = 1800, 1760$.

Nuclear magnetic resonance spectrum (CDCl$_3$): δ (ppm) = 1.40 (3H, s), 2.26 (3H, s), 2.29 (3H, s), 3.45–3.60 (2H, m), 4.60–4.75 (1H, m), 4.82 (1H, s), 4.84 (2H, s), 5.34 (2H, s), 7.61 (2H, d), 8.26 (2H, d).

EXAMPLE 2

Preparation of sodium 2β-(4,5-dimethyl-1,2,3-triazol-1-yl)methyl-2α-methylpenam-3α-carboxylate 1,1-dioxide (Compound 2)

Hydrogenation was conducted at a low pressure (1–5 kg/cm$^2$) and at room temperature in a mixture of 15 ml of ethyl acetate and 15 ml of water using 0.51 g of Compound 1, 0.11 g of 10% palladium charcoal and 0.19 g of sodium hydrogen carbonate. After the absorption of hydrogen ceased, the reaction mixture was filtered. The aqueous layer was separated and washed with ethyl acetate. The aqueous layer was concentrated and the aqueous solution was subjected to column chromatography using MCI gel CHP-20P (product of Mitsubishi Kasei Co., Ltd., Japan) to conduct gradient elution with water-acetone. The eluate thus obtained was freeze-dried to afford 0.27 g of the title compound as a white powder (hereinafter referred to as "Compound 2") which began to decompose at 185° C.

Infrared absorption spectrum (KBr): $v_{max}(\text{cm}^{-1}) = 1780, 1625$.

Nuclear magnetic resonance spectrum (D$_2$O): δ (ppm) = 1.34 (3H, s), 2.25 (3H, s), 2.32 (3H, s), 3.44 (1H, dd), 3.72 (1H, dd), 4.48 (1H, s), 4.95–5.05 (1H, m), 4.98 (1H, d), 5.20 (1H, d).

EXAMPLE 3

Preparation of p-nitrobenzyl 2β-(4,5-di-n-propyl-1,2,3-triazol-1-yl)methyl-2α-methylpenam-3α-carboxylate 1,1-dioxide (Compound 3)

In 10 ml of toluene were refluxed 3.0 g of p-nitrobenzyl 2β-azidomethyl-2α-methylpenam-3α-carboxylate 1,1-dioxide and 2.2 g of 4-octyne with stirring under nitrogen atmosphere for 90 hours. The reaction mixture was concentrated under reduced pressure and the residue was purified by silica gel column chromatography, giving 0.2 g of the title compound as an amorphous product (hereinafter referred to as "Compound 3").

Infrared absorption spectrum (KBr): $\nu_{max}(cm^{-1}) = 1795, 1760$.

Nuclear magnetic resonance spectrum (CDCl$_3$): δ (ppm)=0.95 (6H, t), 1.38 (3H, s), 1.40–1.90 (4H, m), 2.40–2.90 (4H, m), 3.45–3.60 (1H, m), 4.60–4.70 (1H, m), 4.81 (2H, s), 4.90 (1H, s), 5.32 (2H, s), 7.61 (2H, d), 8.27 (2H, d).

EXAMPLE 4

Preparation of p-nitrobenzyl 2β-(4,5-di-n-butyl-1,2,3-triazol-1-yl)methyl-2α-methylpenam-3α-carboxylate 1,1-dioxide (Compound 4)

A 3.0 g quantity of p-nitrobenzyl 2β-azidomethyl-2α-methylpenam-3α-carboxylate 1,1-dioxide, 1.5 g of 5-decyne and 25 ml of benzene were reacted in a sealed tube at 110° C. for 92 hours. The reaction mixture was concentrated under reduced pressure and the residue was purified by silica gel column chromatography, giving 1.1 g of the title compound as an oil (hereinafter referred to as "Compound 4").

Infrared absorption spectrum (NaCl): $\nu_{max}(cm^{-1}) = 1795, 1760$.

Nuclear magnetic resonance spectrum (CDCl$_3$): δ (ppm)=0.93 (6H, t), 1.15–1.90 (8H, m), 1.37 (3H, s), 2.40–2.90 (4H, m), 3.50–3.65 (2H, m), 4.60–4.75 (1H, m), 4.81 (2H, s), 4.89 (1H, s), 5.32 (2H, s), 7.61 (2H, d), 8.26 (2H, d).

EXAMPLE 5

Preparation of sodium 2β-(4,5-di-n-butyl-1,2,3-triazol-1-yl)methyl-2α-methylpenam-3α-carboxylate 1,1-dioxide (Compound 5)

Following the general procedure of Example 2, 0.34 g of the title compound was produced as a white powder from 1.00 g of Compound 4. The white powder began to decompose at 165° C. This compound will be hereinafter referred to as "Compound 5".

Infrared absorption spectrum (KBr): $\nu_{max}(cm^{-1}) = 1785, 1635$.

Nuclear magnetic resonance spectrum (D$_2$O): δ (ppm)=0.89 (3H, t), 0.91 (3H, t), 1.28 (3H, s), 1.1–1.8 (8H, m), 2.5–3.0 (4H, m), 3.3–3.8 (2H, m), 4.45 (1H, s), 4.95–5.05 (1H, m), 5.12 (2H, m).

EXAMPLE 6

Preparation of p-nitrobenzyl 2β-(4-n-butyl-1,2,3-triazol-1-yl)methyl-2α-methylpenam-3α-carboxylate 1,1-dioxide (Compound 6) and p-nitrobenzyl 2β-(5-n-butyl-1,2,3-triazol-1-yl)methyl-2α-methylpenam-3α-carboxylate 1,1-dioxide (Compound 7)

A 3.0 g quantity of p-nitrobenzyl 2β-azidomethyl-2α-methylpenam-3α-carboxylate 1,1-dioxide, 1.2 g of 1-hexyne and 20 ml of benzene were reacted in a sealed tube at 110° C. for 81 hours. The reaction mixture was concentrated under reduced pressure and the residue was subjected to silica gel column chromatography, giving as a first eluted product 1.27 g of a white solid, p-nitrobenzyl 2β-(4-n-butyl-1,2,3-triazol-1-yl)methyl-2α-methylpenam-3αcarboxylate 1,1-dioxide (Compound 6).

Infrared absorption spectrum (KBr): $\nu_{max}(cm^{-1}) = 1805, 1765$.

Nuclear magnetic resonance spectrum (CDCl$_3$): δ (ppm)=0.92 (3H, t), 1.20–1.80 (4H, m), 1.28 (3H, s), 2.60–2.85 (2H, m), 3.45–3.65 (2H, m), 4.68 (1H, s), 4.60–4.75 (1H, m). 5.00 (2H, s), 5.36 (2H, s), 7.49 (1H, s), 7.61 (2H, d), 8.28 (2H, d).

From a second eluate, 0.56 g of p-nitrobenzyl 2β-(5-n-butyl-1,2,3-triazol-1-yl)methyl-2α-methylpenam-3α-carboxylate 1,1-dioxide (Compound 7) was obtained as an oil.

Infrared absorption spectrum (NaCl): $\nu_{max}(cm^{-1}) = 1790, 1755$.

Nuclear magnetic resonance spectrum (CDCl$_3$): δ (ppm)=0.95 (3H, t), 1.20–1.80 (4H, m), 1.41 (3H, s), 2.60–2.85 (2H, m), 3.45–3.60 (2H, m), 4.60–4.75 (1H, m), 4.86 (2H, s), 4.88 (1H, s), 5.33 (2H, s), 7.46 (1H, s), 7.60 (2H, d), 8.26 (2H, d).

EXAMPLE 7

Preparation of sodium 2β-(4-n-butyl-1,2,3-triazol-1-yl)methyl-2α-methylpenam-3α-carboxylate 1,1-dioxide (Compound 8)

Following the general procedure of Example 2, the title compound (0.58 g) was produced as a white powder from 1.00 g of Compound 6. The white powder began to decompose at 185° C. This compound will be hereinafter referred to as "Compound 8".

Infrared absorption spectrum (KBr): $\nu_{max}(cm^{-1}) = 1790, 1635$.

Nuclear magnetic resonance spectrum (D$_2$O): δ (ppm)=0.89 (3H, t), 1.1–1.8 (4H, m), 1.41 (3H, s), 2.72 (2H, t), 3.35–3.83 (2H, m), 4.45 (1H, s), 4.9–5.1 (1H, m) 5.17 (2H, m), 7.88 (1H, s).

EXAMPLE 8

Preparation of sodium 2β-(5-n-butyl-1,2,3-triazol-1-yl)methyl-2α-methylpenam-3α-carboxylate 1,1-dioxide (Compound 9)

Following the general procedure of Example 2, the title compound (0.34 g) was produced as a white powder from 0.56 g of Compound 7. The white powder began to decompose at 185° C. This compound will be hereinafter referred to as "Compound 9".

Infrared absorption spectrum (KBr): $\nu_{max}(cm^{-1}) = 1785, 1630$.

Nuclear magnetic resonance spectrum (D$_2$O): δ (ppm)=0.93 (3H, t), 1.33 (3H, s), 1.2–1.8 (4H, m), 2.78 (2H, t), 3.3–3.8 (2H, m), 4.48 (1H, s), 4.96–5.07 (1H, m), 5.14 (2H, m), 7.66 (1H, s).

EXAMPLE 9

Preparation of p-nitrobenzyl 2β-(5-methyl-1,2,3-triazol-1-yl)methyl-2α-methylpenam-3α-carboxylate 1,1-dioxide (Compound 10)

A 4.00 g quantity of p-nitrobenzyl 2β-azidomethyl-2α-methylpenam-3α-carboxylate 1,1-dioxide, 50 ml of isopropenyl acetate and a small amount of hydroquinone were reacted in a sealed tube at 130° C. for 72 hours. The reaction mixture was concentrated under reduced pressure and the residue was purified by silica gel column chromatography, giving 1.10 g of an amorphous product which will be hereinafter referred to as "Compound 10".

Infrared absorption spectrum (KBr): $\nu_{max}(cm^{-1}) = 1800, 1760$.

Nuclear magnetic resonance spectrum (CDCl$_3$): δ (ppm)=1.43 (3H, s), 2.17 (3H, s), 3.45–3.60 (2H, m), 4.60–4.75 (1H, m), 4.85 (1H, s), 4.87 (2H, s), 5.34 (2H, s), 7.45 (1H, s), 7.60 (2H, d), 8.26 (2H, d).

EXAMPLE 10

Preparation of sodium 2β-(5-methyl-1,2,3-triazol-1-yl)methyl-2α-methylpenam-3α-carboxylate 1,1-dioxide (Compound 11)

Following the general procedure of Example 2, 0.30 g of the contemplated compound was prepared as a yellow powder from 0.50 g of Compound 10. The yellow powder began to decompose at 185° C. This compound will be hereinafter referred to as "Compound 11".

Infrared absorption spectrum (KBr): $v_{max}$(cm$^{-1}$)=1785, 1630.

Nuclear magnetic resonance spectrum (D$_2$O): δ (ppm)=1.36 (3H, s), 2.41 (3H, s), 3.45 (1H, dd), 3.73 (1H, dd), 4.51 (1H, s), 4.95–5.08 (1H, m), 5.14 (2H, m), 7.62 (1H, s).

EXAMPLE 11

Preparation of p-nitrobenzyl 2β-(4-phenyl-1,2,3-triazol-1-yl)methyl-2α-methylpenam-3α-carboxylate 1,1-dioxide (Compound 12) and p-nitrobenzyl 2β-(5-phenyl-1,2,3-triazol-1yl)methyl-2α-methylpenam-3α-carboxylate 1,1-dioxide (Compound 13)

A 3.0 g quantity of p-nitrobenzyl 2β-azidomethyl-2α-methylpenam-3α-carboxylate 1,1-dioxide and 3.0 g of phenylacetylene were refluxed with stirring in 75 ml of benzene under nitrogen atmosphere for 90 hours. The reaction mixture was concentrated under reduced pressure and the residue was subjected to silica gel column chromatography, giving as a first eluted product 0.91 g of a white solid, p-nitrobenzyl 2β-(4-phenyl-1,2,3-triazol-1-yl)methyl-2α-methylpenam-3α-carboxylate 1,1-dioxide (Compound 12) which melted at 212° to 214° C.

Infrared absorption spectrum (KBr): $v_{max}$(cm$^{-1}$)=1800, 1760.

Nuclear magnetic resonance spectrum (DMSO-d$_6$): δ (ppm)=1.42 (3H, s), 3.20–3.50 (1H, m), 3.60–3.90 (1H, m), 4.75–5.60 (6H, m), 7.20–7.90 (7H, s), 8.23 (2H, d), 8.55 (1H, s).

From a second eluate, 0.8 g of p-nitrobenzyl 2β-(5-phenyl-1,2,3-triazol-1-yl)methyl-2α-methylpenam-3α-carboxylate 1,1-dioxide (Compound 13) was obtained as an amorphous product.

Infrared absorption spectrum (KBr): $v_{max}$(cm$^{-1}$)=1800, 1760.

Nuclear magnetic resonance spectrum (CDCl$_3$): δ (ppm)=1.21 (3H, s), 3.40–3.55 (2H, m), 4.50–4.60 (1H, m), 4.95 (2H, s), 5.00 (1H, s), 5.11 (1H, d), 5.31 (1H, d), 7.20–7.60 (7H, m), 7.70 (1H, s), 8.26 (2H, d).

EXAMPLE 12

Preparation of sodium 2β-(4-phenyl-1,2,3-triazol-1-yl)methyl-2α-methylpenam-3α-carboxylate 1,1-dioxide (Compound 14)

Following the general procedure of Example 2, the title compound (0.27 g) was prepared as a white powder from 0.52 g of Compound 12. The white powder began to decompose at 200° C. This compound will be hereinafter referred to as "Compound 14".

Infrared absorption spectrum (KBr): $v_{max}$(cm$^{-1}$)=1775, 1625.

Nuclear magnetic resonance spectrum (D$_2$O): δ (ppm)=1.45 (3H, s), 3.30–3.85 (2H, m), 4.48 (1H, s), 4.95–5.40 (3H, m), 7.35–7.60 (3H, m), 7.70–7.85 (2H, m), 8.35 (1H, s).

EXAMPLE 13

Preparation of sodium 2β-(5-phenyl-1,2,3-triazol-1-yl)methyl-2α-methylpenam-3α-carboxylate 1,1-dioxide (Compound 15)

Following the general procedure of Example 2, the title compound (0.27 g) was prepared as a white powder from 0.52 g of Compound 13. The white powder began to decompose at 195° C. This compound will be hereinafter referred to as "Compound 15".

Infrared absorption spectrum (KBr): $v_{max}$(cm$^{-1}$)=1780, 1625.

Nuclear magnetic resonance spectrum (D$_2$O): δ (ppm)=1.10 (3H, s), 3.25–3.75 (2H, m), 4.33 (1H, s), 4.85–5.00 (1H, m), 5.33 (2H, s), 7.58 (5H, s), 7.90 (1H, s).

EXAMPLE 14

Preparation of p-nitrobenzyl 2β-(4,5-diphenyl-1,2,3-triazol-1-yl)methyl-2α-methylpenam-3α-carboxylate 1,1-dioxide (Compound 16)

A 3.0 g quantity of p-nitrobenzyl 2β-azidomethyl-2α-methylpenam-3α-carboxylate 1,1-dioxide and 3.2 g of diphenylacetylene were reacted under nitrogen atmosphere at 110° C. for 42 hours. The reaction mixture was purified by silica gel column chromatography, giving 2.1 g of an amorphous product. This compound will be hereinafter referred to as "Compound 16".

Infrared absorption spectrum (KBr): $v_{max}$(cm$^{-1}$)=1800, 1760.

Nuclear magnetic resonance spectrum (CDCl$_3$): δ (ppm)=1.36 (3H, s), 3.40–3.55 (2H, m), 4.50–4.70 (1H, m), 4.77 (2H, s), 5.02 (1H, s), 5.05 (1H, d), 5.30 (1H, d), 7.10–7.60 (12H, m), 8.16 (2H, d).

EXAMPLE 15

Preparation of 2β-(4,5-diphenyl-1,2,3-triazol-1-yl)methyl-2α-methylpenam-3α-carboxylic acid 1,1-dioxide (Compound 17)

Hydrogenation was conducted at a low pressure (1–5 kg/cm$^2$) and at room temperature in a mixture of 40 ml of ethyl acetate and 40 ml of water by using 1.20 g of Compound 16, 0.24 g of 10% palladium charcoal and 0.34 g of sodium hydrogen carbonate. After the absorption of hydrogen ceased, the reaction mixture was filtered, and the aqueous layer was separated. The aqueous layer was washed with ethyl acetate, adjusted to a pH of 1.2 with diluted hydrochloric acid, and extracted with ethyl acetate. The organic layer was concentrated under reduced pressure, affording 0.48 g of a white powder. The white powder began to decompose at 170° C. This compound will be hereinafter referred to as "Compound 17".

Infrared absorption spectrum (KBr): $v_{max}$(cm$^{-1}$)=1800, 1750.

Nuclear magnetic resonance spectrum (DMSO-d$_6$): δ (ppm)=1.17 (3H, s), 3.16–3.77 (2H, m), 4.64 (1H, s), 4.73 (1H, d), 5.12 (1H, d), 5.12 (1H, d), 7.2–7.6 (10H, m).

EXAMPLE 16

Preparation of benzhydryl 2β-(4-trifluoromethyl-1,2,3-triazol-1-yl)methyl-2α-methylpenam-3α-carboxylate 1,1-dioxide (Compound 18)

Benzhydryl 2β-azidomethyl-2α-methylpenam-3α-carboxylate 1,1-dioxide (0.3 g), 1.35 g of trifluoromethylacetylene and 3 ml of dichloromethane were reacted in a sealed tube at 55° to 60° C. for 7 days. The reaction mixture was concentrated and the residue was purified by silica gel column chromatography, giving a white solid. This compound will be hereinafter referred to as "Compound 18".

Infrared absorption spectrum (KBr): $\nu_{max}(cm^{-1}) = 1800, 1755$.

Nuclear magnetic resonance spectrum (CDCl$_3$): δ (ppm)=1.06 (3H, s), 3.40–3.60 (2H, m), 4.55–4.70 (1H, m), 4.66 (1H, s), 5.10 (2H, m), 7.02 (1H, s), 7.20–7.50 (10H, m), 8.02 (1H, d).

EXAMPLE 17

Preparation of sodium 2α-methylpenam-2β-(4-trifluoromethyl-1,2,3-triazol-1-yl)methyl-3α-carboxylate 1,1-dioxide (Compound 19)

Following the general procedure of Example 2, the title compound (0.009 g) was prepared as a white powder from 0.030 g of Compound 18. The white powder began to decompose at 185° C. This compound will be hereinafter referred to as "Compound 19".

Infrared absorption spectrum (KBr): $\nu_{max}(cm^{-1}) = 1780, 1630$.

Nuclear magnetic resonance spectrum (D$_2$O): δ (ppm)=1.46 (3H, s), 3.3–3.8 (2H, m), 4.51 (1H, s), 4.9–5.1 (1H, m), 5.32 (2H, m), 8.71 (1H, s).

EXAMPLE 18

Preparation of p-nitrobenzyl 2β-(4-methoxymethyl-1,2,3-triazol-1-yl)methyl-2α-methylpenam-3α-carboxylate 1,1-dioxide (Compound 20) and p-nitrobenzyl 2β-(5-methoxymethyl-1,2,3-triazol-1-yl)methyl-2α-methylpenam-3α-carboxylate 1,1-dioxide (Compound 21)

A 3.0 g quantity of p-nitrobenzyl 2β-azidomethyl-2α-methylpenam-3α-carboxylate 1,1-dioxide was refluxed in 15 ml of methyl propargyl ether under nitrogen atmosphere for 48 hours. The excess methyl propargyl ether was distilled off under reduced pressure and the residue was subjected to silica gel column chromatography, producing as a first eluted product 0.87 g of an oil, p-nitrobenzyl 2β-(5-methoxymethyl-1,2,3-triazol-1-yl)methyl-2α-methylpenam-3α-carboxylate 1,1-dioxide (Compound 21).

Infrared absorption spectrum (NaCl): $\nu_{max}(cm^{-1}) = 1790, 1655$.

Nuclear magnetic resonance spectrum (CDCl$_3$): δ (ppm)=1.52 (3H, s), 3.41 (3H, s), 3.45–3.60 (2H, m), 4.40–4.75 (3H, m), 4.98 (2H, s), 5.08 (1H, s), 5.14 (1H, d), 5.32 (1H, d), 7.55 (2H, d), 7.58 (1H, s), 8.25 (2H, d).

From a second eluate, p-nitrobenzyl 2β-(4-methoxymethyl-1,2,3-triazol-1-yl)methyl-2α-methylpenam-3α-carboxylate 1,1-dioxide (Compound 20) was obtained as a white solid, m.p. 152° to 154° C.

Infrared absorption spectrum (KBr): $\nu_{max}(cm^{-1}) = 1795, 1770$.

Nuclear magnetic resonance spectrum (CDCl$_3$): δ (ppm)=1.31 (3H, s), 3.40 (3H, s), 3.45–3.60 (2H, m), 4.58 (2H, s), 4.65–4.70 (1H, m), 4.66 (1H, m), 5.03 (2H, s), 5.35 (2H, s), 7.60 (2H, d), 7.76 (1H, s), 8.27 (2H, d).

EXAMPLE 19

Preparation of sodium 2β-(5-methoxymethyl-1,2,3-triazol-1-yl)methyl-2α-methylpenam-3α-carboxylate 1,1-dioxide (Compound 22)

Following the general procedure of Example 2, the title compound (0.45 g) was prepared as a white powder from 0.87 g of Compound 21. The white powder began to decompose at 185° C. This compound will be hereinafter referred to as "Compound 22".

Infrared absorption spectrum (KBr): $\nu_{max}(cm^{-1}) = 1785, 1635$.

Nuclear magnetic resonance spectrum (D$_2$O): δ (ppm)=1.35 (3H, s), 3.37–3.80 (2H, m), 3.44 (3H, s), 4.50 (1H, s), 4.72 (2H, s), 4.97–5.08 (1H, m), 5.24 (2H, m), 7.86 (1H, s).

EXAMPLE 20

Preparation of benzhydryl 2β-(4-carbamoyl-1,2,3-triazol-1-yl)methyl-2α-methylpenam-3α-carboxylate 1,1-dioxide (Compound 23) and benzhydryl 2β-(5-carbamoyl-1,2,3-triazol-1-yl)methyl-2α-methylpenam-3α-carboxylate 1,1-dioxide (Compound 24)

A 0.3 g quantity of benzhydryl 2β-azidomethyl-2α-methylpenam-3α-carboxylate 1,1-dioxide, 0.05 g of propiolic amide and 1.5 ml of dichloromethane were reacted in a sealed tube at 90° to 95° C. for 40 hours. The reaction mixture was concentrated under reduced pressure and the residue was subjected to silica gel column chromatography, giving as a first eluted product a white solid, benzhydryl 2β-(4-carbamoyl-1,2,3-triazol-1-yl)methyl-2α-methylpenam-3α-carboxylate 1,1-dioxide (Compound 23).

Infrared absorption spectrum (KBr): $\nu_{max}(cm^{-1}) = 1800, 1750, 1680$.

Nuclear magnetic resonance spectrum (CDCl$_3$): δ (ppm)=1.08 (3H, s), 3.30–3.80 (2H, m), 4.55–4.70 (1H, m), 4.84 (1H, s), 5.06 (2H, bs), 6.47 (1H, bs), 6.98 (1H, s), 7.10–7.50 (11H, m), 8.31 (1H, s).

From a second eluate, benzhydryl 2β-(5-carbamoyl-1,2,3-triazol-1-yl)methyl-2α-methylpenam-3α-carboxylate 1,1-dioxide (Compound 24) was obtained as a white solid.

Infrared absorption spectrum (KBr): $\nu_{max}(cm^{-1}) = 1800, 1745, 1685$.

Nuclear magnetic resonance spectrum (CDCl$_3$): δ (ppm)=1.23 (3H, s), 2.30–2.50 (2H, m), 3.45–3.60 (1H, m), 5.20 (1H, d), 5.33 (1H, s), 5.57 (1H, d), 6.5 (2H, bs), 6.88 (1H, s), 7.15–7.60 (10H, m), 7.90 (1H, s).

EXAMPLE 21

Preparation of benzhydryl
2β-(4-methylcarbamoyl-1,2,3-triazol-1-yl)methyl-2α-methylpenam-3α-carboxylate 1,1-dioxide (Compound 25) and benzhydryl
2β-(5-methylcarbamoyl-1,2,3-triazol-1-yl)methyl-2α-methylpenam-3α-carboxylate 1,1-dioxide (Compound 26)

Following the general procedure of Example 20, and using 1.32 g of benzhydryl 2β-azidomethyl-2α-methylpenam-3α-carboxylate 1,1-dioxide and 0.25 g of N-methylpropiolic amide, benzhydryl 2β-(4-methylcarbamoyl-1,2,3-triazol-1-yl)methyl-2α-methypenam-3α-carboxylate 1,2,3-triazol-1-yl)methyl-2α-methylpenam-3α-carboxylate 1,1-dioxide (Compound 25) was obtained as a white solid and benzhydryl 2β-(5-methylcarbamoyl-1,2,3-triazol-1-yl)methyl-2α-methylpenam-3α-carboxylate 1,1-dioxide (Compound 26) was produced as a white solid.

Compound 25
Infrared absorption spectrum (KBr): $\nu_{max}(cm^{-1}) = 1800, 1755, 1655$.

Nuclear magnetic resonance spectrum (CDCl₃): δ (ppm) = 1,07 (3H, s), 2.99 (3H, d), 3.40–3.60 (2H, m), 4.50–4.65 (1H, m), 4.76 (1H, s), 4.96 (1H, d), 5.13 (1H, d), 7.00 (1H, s), 7.00–7.50 (11H, m), 8.18 (1H, s).

Compound 26
Infrared absorption spectrum (KBr): $\nu_{max}(cm^{-1}) = 1800, 1740, 1670$.

Nuclear magnetic resonance spectrum (CDCl₃): δ (ppm) = 1.25 (3H, s), 2.93 (3H, d), 3.35–3.50 (2H, m), 2.45–2.60 (1H, m), 5.26 (1H, s), 5.26 (1H, d), 5.54 (1H, d), 6.55–6.80 (1H, m), 6.91 (1H, s), 7.20–7.40 (10H, m), 7.80 (1H, s).

EXAMPLE 22

Preparation of benzhydryl
2β-(4-ethylcarbamoyl-1,2,3-triazol-1-yl)methyl-2α-methylpenam-3α-carboxylate 1,1-dioxide (Compound 27) and benzhydryl
2β-(5-ethylcarbamoyl-1,2,3-triazol-1-yl)methyl-2α-methylpenam-3α-carboxylate 1,1-dioxide (Compound 28)

Following the general procedure of Example 20 and using 2 g of benzhydryl 2β-azidomethyl-2α-methylpenam-3α-carboxylate 1,1-dioxide and 0.4 g of N-ethylpropiolic amide, benzhydryl 2β-(4-ethylcarbamoyl-1,2,3-triazol-1-yl)methyl-2α-methylpenam-3α-carboxylate 1,1-dioxide (Compound 27) was obtained as a white solid and benzhydryl 2β-(5-ethylcarbamoyl-1,2,3-triazol-1-yl)methyl-2α-methylpenam-3α-carboxylate 1,1-dioxide (Compound 28) was produced as a white solid.

Compound 27
Infrared absorption spectrum (KBr): $\nu_{max}(cm^{-1}) = 1800, 1750, 1655$.

Nuclear magnetic resonance spectrum (CDCl₃): δ (ppm) = 1.06 (3H, s), 1.23 (3H, t), 3.25–3.65 (4H, m), 4.55–4.70 (1H, m), 4.80 (1H, s), 4.95 (1H, d), 5.13 (1H, d), 6.99 (1H, s), 7.10–7.50 (11H, m), 8.18 (1H, s).

Compound 28
Infrared absorption spectrum (KBr): $\nu_{max}(cm^{-1}) = 1800, 1750, 1670$.

Nuclear magnetic resonance spectrum (CDCl₃): δ (ppm) = 1.20 (3H, t), 1.24 (3H, s), 3.20–3.60 (4H, m), 3.45–3.60 (1H, m), 5.24 (1H, s), 5.27 (1H, d), 5.54 (1H, d), 6.65 (1H, t), 6.91 (1H, s), 7.20–7.40 (10H, s), 7.78 (1H, s).

EXAMPLE 23

Preparation of sodium
2β-(4-ethylcarbamoyl-1,2,3-triazol-1-yl)methyl-2α-methylpenam-3α-carboxylate 1,1-dioxide (Compound 29)

Following the general procedure of Example 2, the title compound (0.011 g) was produced as a yellow powder from 0.052 g of Compound 27. The yellow powder began to decompose at 185° C. This compound will be hereinafter referred to as "Compound 29".

Infrared absorption spectrum (KBr): $\nu_{max}(cm^{-1}) = 1790, 1645$.

Nuclear magnetic resonance spectrum (D₂O): δ (ppm) = 1.23 (3H, t), 1.45 (3H, s), 3.36–3.84 (2H, m), 3.43 (2H, m), 4.50 (1H, s), 4.97–5.07 (1H, m), 5.28 (2H, m), 8.54 (1H, s).

EXAMPLE 24

Preparation of p-nitrobenzyl
2β-(4,5-dicarbamoyl-1,2,3-triazol-1-yl)methyl-2α-methylpenam-3α-carboxylate 1,1-dioxide (Compound 30)

A 1.08 g quantity of p-nitrobenzyl 2β-azidomethyl-2α-methylpenam-3α-carboxylate 1,1-dioxide and 1.18 g of acetylene dicarboxyamide were refluxed in 60 ml of 1,4-dioxane under nitrogen atmosphere for 46 hours. The reaction mixture was concentrated under reduced pressure and the residual powder was washed with chloroform, giving 1.30 g of the desired compound as a yellow powder melting at 117° to 120° C. This compound will be hereinafter referred to as "Compound 30".

Infrared absorption spectrum (KBr): $\nu_{max}(cm^{-1}) = 1800, 1755, 1685$.

Nuclear magnetic resonance spectrum (DMSO-d₆): δ (ppm) = 1.33 (3H, s), 3.25–3.82 (2H, m), 5.12–5.52 (5H, m), 6.01 (1H, d), 7.70 (2H, d), 8.25 (2H, d), 8.57 (2H, s), 10.44 (2H, s).

EXAMPLE 25

Preparation of sodium
2β-(4,5-dicarbamoyl-1,2,3-triazol-1-yl)methyl-2α-methylpenam-3α-carboxylate 1,1-dioxide (Compound 31)

Following the general procedure of Example 2, the title compound (0.20 g) was produced as a white powder from 0.52 g of Compound 30. The white powder began to decompose at 215° C. This compound will be hereinafter referred to as "Compound 31".

Infrared absorption spectrum (KBr): $\nu_{max}(cm^{-1}) = 1780, 1680, 1630$.

Nuclear magnetic resonance spectrum (D₂O): δ (ppm) = 1.43 (3H, s), 3.33–3.82 (2H, m), 4.57 (1H, s), 4.99–5.05 (1H, m), 5.41 (1H, d), 5.91 (1H, d).

EXAMPLE 26

Preparation of p-nitrobenzyl
2β-(4-acetyl-1,2,3-triazol-1-yl)methyl-2α-methylpenam-3α-carboxylate 1,1-dioxide (Compound 32)

A 3.0 g quantity of p-nitrobenzyl 2β-azidomethyl-2α-methylpenam-3α-carboxylate 1,1-dioxide and 1.5 g of 3-butyne-2-one were refluxed with stirring in 70 ml of benzene under nitrogen atmosphere for 17 hours. The reaction mixture was concentrated under reduced pressure and the residue was purified by silica gel column chromatography, giving an amorphous product. This compound will be hereinafter referred to as "Compound 32".

Infrared absorption spectrum (KBr): $\nu_{max}$(cm$^{-1}$)=1800, 1760, 1690.

Nuclear magnetic resonance spectrum (CDCl$_3$): δ (ppm)=1.34 (3H, s), 2.68 (3H, s), 3.50–3.65 (2H, m), 4.60–4.70 (1H, m), 4.67 (1H, s), 5.07 (2H, s), 5.37 (2H, s), 7.60 (2H, d), 8.28 (1H, s), 8.29 (2H, d).

EXAMPLE 27

Preparation of sodium 2β-(4-acetyl-1,2,3-triazol-1-yl)methyl-2α-methylpenam-3α-carboxylate 1,1-dioxide (Compound 33)

Following the general procedure of Example 2, the title compound (0.25 g) was produced as a white powder from 0.48 g of Compound 32. The white powder began to decompose at 195° C. This compound will be hereinafter referred to as "Compound 33".

Infrared absorption spectrum (KBr): $\nu_{max}$(cm$^{-1}$)=1785, 1690, 1630.

Nuclear magnetic resonance spectrum (D$_2$O): δ (ppm)=1.46 (3H, s), 2.67 (3H, s), 3.52–3.84 (2H, m), 4.51 (1H, s), 4.98–5.08 (1H, m), 5.30 (2H, m), 8.76 (1H, s).

EXAMPLE 28

Preparation of benzhydryl 2β-(4-cyano-1,2,3-triazol-1-yl)methyl-2α-methylpenam-3α-carboxylate 1,1-dioxide (Compound 34)

A 1 g quantity of benzhydryl 2β-azidomethyl-2α-methylpenam-3α-carboxylate 1,1-dioxide, 0.33 g of monocyanoacetylene and 3.5 ml of dichloromethane were reacted in a sealed tube at 70° to 80° C. for 20 hours. The reaction mixture was concentrated under reduced pressure and residue was purified by silica gel column chromatography, giving a white solid. This compound will be hereinafter referred to as "Compound 34".

Infrared absorption spectrum (KBr): $\nu_{max}$(cm$^{-1}$)=2250, 1800, 1750. Nuclear magnetic resonance spectrum (CDCl$_3$): δ (ppm)=1.06 (3H, s), 3.45–3.60 (2H, m), 4.62 (1H, s), 4.60–4.70 (1H, m), 5.12 (2H, s), 7.03 (1H, s), 7.20–7.50 (10H, m), 8.19 (1H, s).

EXAMPLE 29

Preparation of p-nitrobenzyl 2β-(4-allyloxycarbonyl-1,2,3-triazol-1-yl)methyl-2α-methylpenam-3α-carboxylate 1,1-dioxide (Compound 35) and p-nitrobenzyl 2β-(5-allyloxycarbonyl-1,2,3-triazol-1-yl)methyl-2α-methylpenam-3α-carboxylate 1,1-dioxide (Compound 36)

A 3 g quantity of p-nitrobenzyl 2β-azidomethyl-2α-methylpenam-3α-carboxylate 1,1-dioxide and 2.2 g of allyl propiolate were refluxed in 60 ml of benzene under nitrogen atmosphere for 30 hours. The reaction mixture was concentrated under reduced pressure and the residue was subjected to silica gel column chromatography, affording as a first eluted product 0.6 g of an oil, p-nitrobenzyl 2β-(5-allyloxycarbonyl-1,2,3-triazol-1-yl)methyl-2α-methylpenam-3α-carboxylate 1,1-dioxide (Compound 36).

Infrared absorption spectrum (NaCl): $\nu_{max}$(cm$^{-1}$)=1800, 1760, 1730. Nuclear magnetic resonance spectrum (CDCl$_3$): δ (ppm)=1.39 (3H, s), 3.45–3.60 (2H, m), 4.55–4.70 (1H, m), 4.70–4.90 (2H, m), 5.10 (1H, s), 5.15–6.20 (7H, m), 7.53 (2H, d), 8.11 (1H, s), 8.25 (2H, d).

From a second eluate, 1.4 g of p-nitrobenzyl 2β-(4-allyloxycarbonyl-1,2,3-triazol-1-yl)methyl-2α-methylpenam-3α-carboxylate 1,1-dioxide (Compound 35) was obtained as an oil.

Infrared absorption spectrum (NaCl): $\nu_{max}$(cm$^{-1}$)=1800, 1740.

Nuclear magnetic resonance spectrum (CDCl$_3$): δ (ppm)=1.34 (3H, s), 3.50–3.65 (2H, m), 4.60–4.75 (1H, m), 4.69 (1H, s), 4.75–4.90 (2H, m), 5.10 (2H, s), 5.15–6.20 (3H, m), 5.36 (2H, s), 7.60 (2H, d), 8.27 (2H, d), 8.32 (1H, s).

EXAMPLE 30

Preparation of p-nitrobenzyl-2α-methyl-2β-(4-propargyloxycarbonyl-1,2,3-triazol-1-yl)methylpenam-3α-carboxylate 1,1-dioxide (Compound 37) and p-nitrobenzyl 2α-methyl-2β-(5-propargyloxycarbonyl-1,2,3-triazol-1-yl)methylpenam-3α-carboxylate 1,1-dioxide (Compound 38)

A 3.21 g quantity of p-nitrobenzyl 2β-azidomethyl-2α-methylpenam-3α-carboxylate 1,1-dioxide and 2.60 g of propargyl propiolate were refluxed in 100 ml of benzene under nitrogen atmosphere for 20 hours. The reaction mixture was concentrated under reduced pressure and the residue was subjected silica gel column chromatography, giving as a first eluted product 0.28 g of an oil, p-nitrobenzyl 2α-methyl-2β-(5-propargyloxycarbonyl-1,2,3-triazol-1-yl)methylpenam-3α-carboxylate 1,1-dioxide (Compound 38).

Infrared absorption spectrum (NaCl): $\nu_{max}$(cm$^{-1}$)=1800, 1740. Nuclear magnetic resonance spectrum (CDCl$_3$): δ (ppm)=2.17 (3H, s), 2.61 (1H, t), 3.52–3.57 (2H, m), 4.64–4.70 (1H, m), 4.92 (2H, d), 5.07 (1H, s), 5.25 (2H, d), 5.19–5.63 (2H, m), 7.55 (2H, d), 8.14 (1H, s), 8.25 (2H, d).

From a second eluate, 0.62 g of p-nitrobenzyl 2α-methyl-2β-(4-propargyloxycarbonyl-1,2,3-triazol-1-yl)methylpenam-3α-carboxylate 1,1-dioxide (Compound 37) was obtained as an amorphous product.

Infrared absorption spectrum (KBr): $\nu_{max}$(cm$^{-1}$)=1800, 1740.

Nuclear magnetic resonance spectrum (CDCl$_3$): δ (ppm)=1.26 (3H, s), 2.55 (1H, t), 3.56–3.62 (2H, m), 4.68 (1H, s), 4.68–4.75 (1H, m), 4.95 (2H, m), 5.11 (2H, s), 5.36 (2H, s), 7.60 (2H, d), 8.27 (2H, d), 8.35 (1H, s).

EXAMPLE 31

Preparation of p-nitrobenzyl 2β-(4,5-diallyloxycarbonyl-1,2,3-triazol-1yl)methyl-2α-methylpenam-3α-carboxylate 1,1-dioxide (Compound 39)

A 3 g quantity of p-nitrobenzyl 2β-azidomethyl-2α-methylpenam-3α-carboxylate 1,1-dioxide and 2.8 g of dially acetylenedicarboxylate were refluxed with stirring in 70 ml of benzene under nitrogen atmosphere for 20 hours. The reaction mixture was concentrated under reduced pressure and the residue was purified by silica gel column chromatography, giving 3.8 g of the title compound as an amorphous product. This compound will be hereinafter referred to as "Compound 39".

Infrared absorption spectrum (KBr): $\nu_{max}$(cm$^{-1}$)=1805, 1730.

Nuclear magnetic resonance spectrum (CDCl$_3$): δ (ppm)=1.43 (3H, s), 3.45-3.60 (2H, m), 3.55-3.70 (1H, m), 3.75-3.90 (4H, m), 5.02 (1H, s), 5.10-6.20 (10H, m), 7.53 (2H, d), 8.24 (2H, d).

EXAMPLE 32

Preparation of p-nitrobenzyl 2β-(4,5-dipropargyloxycarbonyl-1,2,3-triazol-1-yl)methyl-2α-methylpenam-3α-carboxylate 1,1-dioxide (Compound 40)

A 3.66 g quantity of p-nitrobenzyl 2β-azidomethyl-2α-methylpenam-3α-carboxylate 1,1-dioxide and 3.40 g of dipropargyl acetylenedicarboxylate were refluxed in 100 ml of benzene under nitrogen atmosphere for 24 hours. The reaction mixture was concentrated under reduced pressure and the residue was purified by silica gel column chromatography, giving 4.81 g of the title compound as an oil. This compound will be hereinafter referred to as "Compound 40".

Infrared absorption spectrum (NaCl): $v_{max}$(cm$^{-1}$)=1800, 1740.

Nuclear magnetic resonance spectrum (CDCl$_3$): δ (ppm)=1.42 (3H, s), 2.58 (1H, t), 2.62 (1H, t), 3.5-3.6 (2H, m), 4.6-4.7 (1H, m), 4.97 (2H, d), 4.98 (2H, d), 4.99 (1H, s), 5.2-5.3 (4H, m), 7.55 (2H, d), 8.25 (2H, d).

EXAMPLE 23

Preparation of benzhydryl 2β-(4-formyl-1,2,3-triazol-1-yl)methyl-2α-methylpenam-3α-carboxylate 1,1-dioxide (Compound 41)

A 0.1 g quantity of benzhydryl 2β-azidomethyl-2α-methylpenam-3α-carboxylate 1,1-dioxide and 0.2 ml of propargyl aldehyde were stirred at room temperature under nitrogen atmosphere for 20 hours. The reaction mixture was concentrated under reduced pressure and the residue was purified by silica gel column chromatography, giving 0.8 g of the title compound as a white solid. This compound will be hereinafter referred to as "Compound 41".

Infrared absorption spectrum (KBr): $v_{max}$(cm$^{-1}$)=1790, 1740, 1690.

Nuclear magnetic resonance spectrum (CDCl$_3$): δ (ppm)=1.09 (3H, t), 3.25-3.65 (2H, m), 4.50-4.67 (1H, m), 4.67 (1H, s), 5.11 (2H, s), 7.02 (1H, s), 7.20-7.50 (10H, m), 8.26 (1H, s), 10.13 (1H, s).

EXAMPLE 34

Preparation of p-nitrobenzyl 2β-(4-ethoxycarbonyl-5-phenyl-1,2,3-triazol-1-yl)methyl-2α-methylpenam-3α-carboxylate 1,1-dioxide (Compound 42) and p-nitrobenzyl 2β-(5-ethoxycarbonyl-4-phenyl-1,2,3-triazol-1-yl)methyl-2α-methylpenam-3α-carboxylate 1,1-dioxide (Compound 43)

A 3.14 g quantity of p-nitrobenzyl 2β-azidomethyl-2α-methylpenam-3α-carboxylate 1,1-dioxide and 2.60 g of ethyl phenylpropiolate were refluxed with stirring in 10 ml of benzene under nitrogen atmosphere for 48 hours. The reaction mixture was concentrated under reduced pressure and the residue was subjected to silica gel column chromatography, giving as a first eluted product 1.43 g of a white solid, p-nitrobenzyl 2β-(5-ethoxycarbonyl-4-phenyl-1,2,3-triazol-1-yl)methyl-2α-methylpenam-3α-carboxylate 1,1-dioxide (Compound 43) melting at 73° to 81° C.

Infrared absorption spectrum (KBr): $v_{max}$(cm$^{-1}$)=1810, 1770, 1730.

Nuclear magnetic resonance spectrum (CDCl$_3$): δ (ppm)=1.26 (3H, t), 1.49 (3H, s), 3.55 (2H, d), 4.35 (2H, m), 4.67 (1H, m), 5.10 (1H, d), 5.16 (1H, s), 5.24 (1H, d), 5.29 (1H, d), 5.54 (1H, d), 7.38-7.52 (5H, m), 7.58-7.72 (2H, m), 8.15 (2H, d).

From a second eluate, 1.42 g of p-nitrobenzyl 2β-(4-ethoxycarbonyl-5-phenyl-1,2,3-triazol-1-yl)methyl-2α-methylpenam-3α-carboxylate 1,1-dioxide (Compound 42) was obtained as a pale yellow solid melting at 99° to 106° C.

Infrared absorption spectrum (KBr): $v$max(cm$^{-1}$)=1810, 1770, 1730.

Nuclear magnetic resonance spectrum (CDCl$_3$): δ (ppm)=1.24 (3H, t), 1.28 (3H, s), 3.43-3.49 (2H, m), 4.29 (2H, m), 4.58 (1H, m), 4.84 (2H, s), 4.93 (1H, s), 5.11 (1H, d), 5.31 (1H, d), 7.26-7.37 (2H, m), 7.49-7.58 (5H, m), 8.26 (2H, d).

EXAMPLE 35

Preparation of sodium 2β-(4-ethoxycarbonyl-5-phenyl-1,2,3-triazol-1-yl)methyl-2α-methylpenam-3α-carboxylate 1,1-dioxide (Compound 44)

Hydrogenation was conducted at a low pressure (1-5 kg/cm$^2$) and at room temperature in a mixture of 30 ml of ethyl acetate and 30 ml of water, using 1.40 g of p-nitrobenzyl 2β-(4-ethoxycarbonyl-5-phenyl-1,2,3-triazol-1-yl)methyl-2α-methylpenam-3α-carboxylate 1,1-dioxide (Compound 42), 0.28 g of 10% palladium charcoal and 0.24 g of sodium hydrogen carbonate. After the absorption of hydrogen ceased, the reaction mixture was filtered and the aqueous layer was separated. The aqueous layer was washed with ethyl acetate, concentrated and subjected to column chromatography using MCI gel CHP-20P (product of Mitsubishi Kasei Co., Ltd., Japan) to conduct gradient elution with water-acetone. The eluate thus obtained was freeze-dried to afford 0.64 g of the title compound as a white powder which decomposed at 188° to 190° C.

Infrared absorption spectrum (KBr): $v_{max}$(cm$^{-1}$)=1780, 1720, 1630.

Nuclear magnetic resonance spectrum (D$_2$O): δ (ppm)=1.16 (3H, s), 1.23 (3H, t), 3.28-3.78 (2H, m), 4.20-4.41 (2H, m), 4.30 (1H, s), 4.93-4.99 (1H, m), 5.10 (1H, d), 5.31 (1H, d), 7.48-7.68 (5H, m).

EXAMPLE 36

Preparation of sodium 2β-(5-ethoxycarbonyl-4-phenyl-1,2,3-triazol-1-yl)methyl-2α-methylpenam-3α-carboxylate 1,1-dioxide (Compound 45)

Following the general procedure of Example 2, the title compound (0.73 g) was produced as a white powder from 1.20 g of p-nitrobenzyl 2β-(5-ethoxycarbonyl-4-phenyl-1,2,3-triazol-1-yl)methyl-2α-methylpenam-3α-carboxylate 1,1-dioxide (Compound 43). The white powder decomposed at 176° to 179° C.

Infrared absorption spectrum (KBr): $v_{max}$(cm$^{-1}$)=1780, 1720, 1630.

Nuclear magnetic resonance spectrum (D$_2$O): δ (ppm)=1.26 (3H, t), 1.47 (3H, s), 3.32-3.50 (1H, m), 3.61-3.80 (1H, m), 4.39 (2H, m), 4.57 (1H, s), 4,91-5.04 (1H, m), 5.51 (1H, d), 5.77 (1H, d), 7.40-7.77 (5H, m).

EXAMPLE 37

Preparation of p-nitrobenzyl
2β-(4,5-diacetoxymethyl-1,2,3-triazol-1-yl)methyl-2α-methylpenam-3α-carboxylate 1,1-dioxide (Compound 46)

A 3 g quantity of p-nitrobenzyl 2β-azidomethyl-2α-methylpenam-3α-carboxylate 1,1-dioxide, 2.5 g of 1,4-diacetoxy-2-butyne and 5 ml of benzene were reacted in a sealed tube at 110° C. for 92 hours. The reaction mixture was concentrated under reduced pressure and the residue was purified by silica gel column chromatography, giving 3.9 g of the title compound as an amorphous product.

Infrared absorption spectrum (KBr): $\nu_{max}(\text{cm}^{-1}) = 1800, 1735$.

Nuclear magnetic resonance spectrum (CDCl$_3$): δ(ppm)=1.46 (3H, s), 2.07 (6H, s), 3.40–3.60 (2H, m), 4.68 (1H, m), 4.85 (1H, s), 4.85–5.30 (2H, m), 5.24 (2H, s), 5.34 (4H, s), 7.60 (2H, d), 8.27 (2H, d).

EXAMPLE 38

Preparation of sodium-2β-(4,5-diacetoxymethyl-1,2,3-triazol-1-yl)methyl-2α-methylpenam-3α-carboxylate 1,1-dioxide (Compound 47)

Following the general procedure of Example 35, the title compound (2.58 g) was prepared as a white powder from 3.60 g of p-nitrobenzyl 2β-(4,5-diacetoxymethyl-1,2,3-triazol-1-yl)methyl-2α-methylpenam-3α-carboxylate 1,1-dioxide (Compound 46). The white powder decomposed at 153° to 155° C.

Infrared absorption spectrum (KBr): $\nu_{max}(\text{cm}^{-1}) = 1785, 1745, 1630$.

Nuclear magnetic resonance spectrum (D$_2$O): δ (ppm)=1.38 (3H, s), 2.11 (3H, s), 2.13 (3H, s), 3.33–3.81 (2H, m), 4.47 (1H, s), 5.00–5.08 (1H, m), 4.95–5.40 (2H, m), 5.30 (2H, s), 5.39 (2H, s).

EXAMPLE 39

Preparation of p-nitrobenzyl
2β-(4,5-dibenzyloxymethyl-1,2,3-triazol-1-yl)methyl-2α-methylpenam-3α-carboxylate 1,1-dioxide (Compound 48)

A 6.0 g quantity of p-nitrobenzyl 2β-azidomethyl-2α-methylpenam-3α-carboxylate 1,1-dioxide, 8 g of 1,4-dibenzyloxy-2-butyne and 5 ml of benzene were reacted in a sealed tube at 110° C. for 95 hours. The reaction mixture was concentrated under reduced pressure and the residue was purified by silica gel column chromatography, giving 7.5 g of the title compound as an amorphous product.

Infrared absorption spectrum (KBr): $\nu_{max}(\text{cm}^{-1}) = 1795, 1755$.

Nuclear magnetic resonance spectrum (CDCl$_3$): δ (ppm)=1.50 (3H, s), 3.40–3.60 (2H, m), 4.49 (2H, s), 4.56 (4H, s), 4.60–4.70 (3H, m), 4.95 (2H, s), 5.12 (1H, s), 5.17 (2H, m), 7.29 (5H, s), 7.32 (5H, s), 7.49 (2H, d), 8.18 (2H, d).

EXAMPLE 40

Preparation of 2β-(4,5-dibenzyloxymethyl-1,2,3-triazol-1-yl)methyl-2α-methylpenam-3α-carboxylic acid 1,1-dioxide (Compound 49)

Hydrogenation was carried out at a low pressure (1–5 kg/cm$^2$) and at room temperature in a mixture of 38 ml of ethyl acetate and 38 ml of water using 5.6 g of p-nitrobenzyl 2β-(4,5-dibenzyloxymethyl-1,2,3-triazol-1-yl)methyl-2α-methylpenam-3α-carboxylate 1,1-dioxide (Compound 48), 1.2 g of 10% palladium charcoal and 0.67 g of sodium hydrogen carbonate. After the absorption of hydrogen ceased, the reaction mixture was filtered and the aqueous layer was separated. The aqueous layer was washed with ethyl acetate, adjusted to a pH of 1.5 and extracted with ethyl acetate. The extract was concentrated under reduced pressure, giving 2.7 g of the title compound as a white powder. The compound decomposed at 158° to 160° C.

Infrared absorption spectrum (KBr): $\nu_{max}(\text{cm}^{-1}) = 1790, 1715$.

Nuclear magnetic resonance spectrum (DMSO-d$_6$): δ (ppm)=1.39 (3H, s), 3.10–3.90 (2H, m), 4.46 (2H, s), 4.51 (2H, s), 4.60 (2H, s), 4.60–4.90 (2H, m), 4.89 (1H, s), 4.90–5.35 (3H, m), 7.30 (5H, s), 13.00 (1H, bs).

EXAMPLE 41

Preparation of sodium
2β-(4,5-dihydroxymethyl-1,2,3-triazol-1-yl)methyl-2α-methylpenam-3α-carboxylate 1,1-dioxide (Compound 50)

Hydrogenation was performed at a low pressure (1–5 kg/cm$^2$) and at room temperature for 9.5 hours in 100 ml of ethanol using 2.0 g of 2β-(4,5-dibenzyloxymethyl-1,2,3-triazol-1-yl)methyl-2α-methylpenam-3α-carboxylate 1,1-dioxide (Compound 49) and 0.86 g of 10% palladium charcoal. The reaction mixture was filtered and the filtrate was concentrated under reduced pressure. The residue was dissolved in an aqueous solution of sodium hydrogen carbonate and the aqueous solution was subjected to column chromatography using MCI gel CHP-20P (product of Mitsubishi Kasei Co., Ltd., Japan) to conduct elution with water. The eluate thus obtained was freeze-dried, giving 0.4 g of the title compound as a white powder. The white powder decomposed at 165° to 169° C.

Infrared absorption spectrum (KBr): $\nu_{max}(\text{cm}^{-1}) = 1775, 1620$.

Nuclear magnetic resonance spectrum (D$_2$O): δ (ppm)=1.36 (3H, s), 3.35–3.85 (2H, m), 4.52 (1H, s), 4.77 (2H, s), 4.87 (1H, s), 5.05 (1H, m), 5.26 (2H, s).

EXAMPLE 42

Preparation of p-nitrobenzyl
2β-(4-ethoxycarbonyl-5-methyl-1,2,3-triazol-1-yl)methyl-2α-methylpenam-3α-carboxylate 1,1-dioxide (Compound 51) and p-nitrobenzyl
2β-(5-ethoxycarbonyl-4-methyl-1,2,3-triazol-1-yl)methyl-2α-methylpenam-3α-carboxylate 1,1-dioxide (Compound 52)

The same procedure as in Example 34 was repeated except that ethyl methylpropiolate was used in place of the ethyl phenylpropiolate employed in Example 34, producing the title compounds, p-nitrobenzyl 2β-(4-ethoxycarbonyl-5-methyl-1,2,3-triazol-1-yl)methyl-2α-methylpenam-3α-carboxylate 1,1-dioxide (Compound 51) and p-nitrobenzyl 2β-(5-ethoxycarbonyl-4-methyl-1,2,3-triazol-1-yl)methyl-2α-methylpenam-3α-carboxylate 1,1-dioxide (Compound 52)

EXAMPLE 43

Preparation of benzhydryl 2β-(4-benzyloxycarbonylamino-1,2,3-triazol-1-yl)methyl-2α-methylpenam-3α-carboxylate 1,1-dioxide (Compound 53)

A 0.25 g quantity of benzhydryl 2β-(4-carboxy-1,2,3-triazol-1-yl)methyl-2α-methylpenam-3α-carboxylate 1,1-dioxide was dissolved in 15 ml of dichloromethane. The solution was ice-cooled. To the stirred ice-cold solution was added a solution of 1.23 ml of triethylamine in 5 ml of dichloromethane with ice-cooling. To the mixture was added at the same temperature a solution of 2.20 ml of oxalyl chloride in 5 ml of dichloromethane. The resulting mixture was stirred at 0° C. for 2 hours and then at room temperature for 30 minutes. To the reaction mixture was added a solution of 0.213 g of tetrabutylammonium azide in 10 ml of benzene over a period of 30 minutes and the mixture was stirred for 3 hours. Benzyl alcohol (0.163 g) was added thereto and the mixture was refluxed under nitrogen atmosphere in an oil bath at 160° C. for 2 hours. The reaction mixture was left to stand overnight at room temperature under nitrogen atmosphere. The resulting reaction mixture was poured into 150 ml of water and the mixture was extracted three times with dichloromethane. The combined organic layers were washed three times with water, dried over magnesium sulfate and filtered. The filtrate was concentrated under reduced pressure, giving a viscous brown solid. The solid was dissolved in dichloromethane, and the solution was washed with a 3% aqueous solution of sodium bicarbonate, dried over magnesium sulfate and filtered. The filtrate was concentrated under reduced pressure. The residue was purified by silica gel column chromatography, giving 67.3 mg of the contemplated compound. The compound thus obtained was recrystallized from ether-hexane-ethyl acetate, affording 36.3 mg of the title compound as white crystals. M.p. 78° to 80° C.

Infrared absorption spectrum (KBr): $\nu_{max}(cm^{-1})=1805, 1740$.

Nuclear magnetic resonance spectrum (CDCl$_3$): δ (ppm)=1.04 (3H, s), 3.52–3.57 (2H, m), 4.59–4.65 (1H, m), 4.64 (1H, s), 5.09 (2H, s), 5.39 (2H, m), 7.01 (1H, s), 7.26–7.50 (10H, m), 8.23 (1H, s).

EXAMPLE 44

Preparation of benzhydryl 2β-(4-ethoxycarbonylamino-1,2,3-triazol-1-yl)methyl-2α-methylpenam-3α-carboxylate 1,1-dioxide (Compound 54)

The title compound was prepared by repeating the same procedure as in Example 43 except that ethanol was used in place of the benzyl alcohol emplolyed in Example 43.

Infrared absorption spectrum (KBr): $\nu_{max}(cm^{-1})=1805, 1745$.

Nuclear magnetic resonance spectrum (CDCl$_3$): δ (ppm)=1.06 (3H, s), 1.41 (3H, t), 3.38–3.67 (2H, m), 4.43 (2H, q), 4.6–4.7 (1H, m), 4.64 (1H, s), 5.11 (2H, m), 7.02 (1H, s), 7.26–7.41 (10H, m), 8.24 (1H, s).

EXAMPLE 45

Preparation of 2β-(4-amino-1,2,3-triazol-1-yl)methyl-2α-methylpenam-3α-carboxylic acid 1,1-dioxide (Compound 55)

Hydrogenation was conducted at a low pressure (1–5 kg/cm$^2$) and at room temperature in a mixture of 20 ml of ethyl acetate and 20 ml of water using 0.070 g of benzhydryl 2β-(4-benzyloxycarbonylamino-1,2,3-triazol-1-yl)methyl-2α-methylpenam-3α-carboxylate 1,1-dioxide and 0.014 g of 10% palladium charcoal. After the absorption of hydrogen ceased, the reaction mixture was filtered and the aqueous layer was separated. The aqueous layer was washed with ethyl acetate and freeze-dried, giving 0.030 g of a white powder. M.p. 180° C. or higher (decomposition).

Infrared absorption spectrum (KBr): $\nu_{max}(cm^{-1})=1795, 1735$.

Nuclear magnetic resonance spectrum (D$_2$O): δ (ppm)=1.47 (3H, s), 3.39–3.84 (2H, m), 4.75 (1H, s), 5.06–5.10 (1H, m), 5.28 (2H, m), 8.69 (1H, s).

The compounds obtained in some of the Examples were checked for β-lactamase inhibitory activity in the following manner.

Test for β-lactamase inhibitory activity

The inhibitory activity against penicillinase (β-lactamase) derived from Bacillus sp. was measured by microiodometry Tanpakushitsu Kakusan Koso (Protein Nucleic Acid Enzyme), vol. 23, No. 5, pp 391 to 400 (1978) using penicillin G as a substrate. Table 1 below shows the results.

TABLE 1

| Compound | 50% Inhibitory Concentration |
|---|---|
| Compound 2 | $8.0 \times 10^{-8}$ M |
| Compound 5 | $3.0 \times 10^{-6}$ M |
| Compound 8 | $2.3 \times 10^{-7}$ M |
| Compound 9 | $6.5 \times 10^{-7}$ M |
| Compound 11 | $2.4 \times 10^{-7}$ M |
| Compound 14 | $4.0 \times 10^{-8}$ M |
| Compound 15 | $2.8 \times 10^{-7}$ M |
| Compound 17 | $2.7 \times 10^{-7}$ M |
| Compound 19 | $2.4 \times 10^{-7}$ M |
| Compound 22 | $1.8 \times 10^{-6}$ M |
| Compound 29 | $2.0 \times 10^{-8}$ M |
| Compound 31 | $1.3 \times 10^{-7}$ M |
| Compound 32 | $1.2 \times 10^{-7}$ M |
| Compound 44 | $4.0 \times 10^{-7}$ M |
| Compound 45 | $1.0 \times 10^{-7}$ M |
| Compound 47 | $2.5 \times 10^{-6}$ M |
| Compound 49 | $1.5 \times 10^{-6}$ M |
| Compound 50 | $2.0 \times 10^{-6}$ M |
| Compound 55 | $7.0 \times 10^{-7}$ M |

Given below are examples of preparation of the present antibacterial compositions.

| Preparation Example 1 | |
|---|---|
| Ampicillin | 200 mg |
| Compound 66 | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

| Preparation Example 2 | |
|---|---|
| Amoxycillin | 100 mg |
| Compound 2 | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

| Preparation Example 3 | |
|---|---|
| Pivmecillinam | 70 mg |
| Compound 11 | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |
| Total | 220 mg |
| | (amount per tablet) |

The above ingredients are formulated in the proportions listed above into a tablet.

| Preparation Example 4 | |
|---|---|
| Compound 29 | 120 mg |
| Hydroxypropyl cellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

We claim:

1. A penicillin derivative of the formula

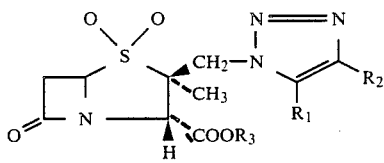

wherein $R_1$ and $R_2$ are the same or different and represent hydrogen, $C_{1-6}$ alkyl, $C_{1-6}$ hydroxyalkyl, $C_{3-9}$ acyloxyalkyl, $C_{8-13}$ benzyloxyalkyl, $C_{2-7}$ alkoxyalkyl, phenyl, amino, cyano, formyl, trifluoromethyl, $C_{2-6}$ acyl, carbamoyl, $C_{2-7}$ alkylcarbamoyl, benzyloxycarbonylamino, $C_{2-7}$ alkoxycarbonylamino; and $R_3$ is hydrogen, a group for forming a pharmaceutically acceptable salt, or a penicillin carboxyl protecting group; with the proviso that both of $R_1$ and $R_2$ are not hydrogen at the same time, or a pharmaceutically acceptable acid addition salt thereof.

2. A compound as defined in claim 1 wherein $R_1$ and $R_2$ are the same or different and represent hydrogen, $C_{1-6}$ alkyl, $C_{2-7}$ alkoxyalkyl, phenyl, cyano, formyl, trifluoromethyl, $C_{2-6}$ acyl, carbamoyl or $C_{2-7}$ alkylcarbamoyl.

3. A compound as defined in claim 1 wherein $R_1$ and $R_2$ are the same or different and represent $C_{1-6}$ alkyl, $C_{1-6}$ hydroxyalkyl, $C_{3-9}$ acyloxyalkyl, $C_{8-13}$ benzyloxyalkyl, or phenyl.

4. A compound as defined in claim 1 wherein one of $R_1$ and $R_2$ is hydrogen and the other is amino, $C_{2-7}$ alkoxycarbonylamino or benzyloxycarbonylamino.

5. A compound as defined in claim 1 wherein $R_1$ and $R_2$ are the same or different and represent hydrogen, $C_{1-6}$ alkyl, $C_{1-6}$ hydroxyalkyl, amino, carbamoyl, $C_{2-7}$ alkylcarbamoyl or $C_{2-6}$ acyl.

6. A pharmaceutical composition for treating bacterial infections in mammals which comprises (A) a β-lactam antibiotic, (B) a penicillin derivative of the formula

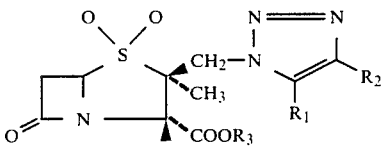

wherein $R_1$ and $R_2$ are the same or different and represent hydrogen, $C_{1-6}$ alkyl, $C_{1-6}$ hydroxyalkyl, $C_{3-9}$ acyloxyalkyl, $C_{8-13}$ benzyloxyalkyl, $C_{2-7}$ alkoxyalkyl, phenyl, amino, cyano, formyl, trifluoromethyl, $C_{2-6}$ acyl, carbamoyl, $C_{2-7}$ alkylcarbamoyl, benzyloxycarbonylamino, $C_{2-7}$ alkoxycarbonylamino; and $R_3$ is hydrogen, a group for forming a pharmaceutically acceptable salt, or a penicillin carboxyl protecting group; with the proviso that both of $R_1$ and $R_2$ are not hydrogen at the same time, and (C) a pharmaceutically acceptable, non-toxic carrier.

7. A pharmaceutical composition as defined in claim 6 wherein the weight ratio of (A)/(B) is about 0.1 to about 10.

8. A pharmaceutical composition as defined in claim 6 wherein the weight ratio of (A)/(B) is about 0.2 to about 5.

9. A pharmaceutical composition as defined in claim 6 wherein the β-lactam antibiotic is ampicillin, amoxicillin, hetacillin, ciclacillin, mecillinam, carbenicillin, sulbenicillin, ticarcillin, piperacillin, apalcillin, methicillin, mezlocillin, bacampicillin, carindacillin, talampicillin, carfecillin, pivmecillinam, cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil, cephaloglycin, or a pharmaceutically acceptable salt thereof.

10. A pharmaceutical composition for inhibiting β-lactamase comprising a compound of the formula

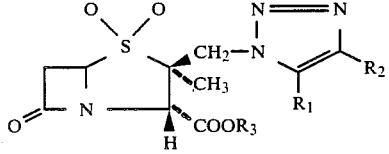

wherein $R_1$ and $R_2$ are the same or different and represent hydrogen, $C_{1-6}$ alkyl, $C_{1-6}$ hydroxyalkyl, $C_{3-9}$ acyloxyalkyl, $C_{8-13}$ benzyloxyalkyl, $C_{2-7}$ alkoxyalkyl, phenyl, amino, cyano, formyl, trifluoromethyl, $C_{2-6}$ acyl, carbamoyl, $C_{2-7}$ alkylcarbamoyl, benzyloxycarbonylamino, $C_{2-7}$ alkoxycarbonylamino; and $R_3$ is hydrogen, a group for forming a pharmaceutically acceptable salt, or a penicillin carboxyl protecting group; with the proviso that both of $R_1$ and $R_2$ are not hydrogen at the same time, in combination with pharmaceutically acceptable, non-toxic carrier.

11. A method for treating bacterial infections in mammals said method comprising administering to a mammal in need of such treatment a therapeutically effective amount of a derivative as claimed in claim 1.

12. A method for treating bacterial infections in mammals, said method comprising administering to a mammal in need of such treatment a therapeutically effective amount of a composition as claimed in claim 6.

13. A method for inhibiting $\beta$-lactamase in a patient in need of such treatment, said method comprising administering to said patient a therapeutically effective amount of a derivative as claimed in claim 1.

14. A method for inhibiting $\beta$-lactamase in a patient in need of such treatment, said method comprising administering to said patient a therapeutically effective amount of a composition as claimed in claim 10.

* * * * *